(12) United States Patent
Levenberg

(10) Patent No.: US 11,468,785 B2
(45) Date of Patent: Oct. 11, 2022

(54) SYSTEM AND METHOD FOR MULTI-STAGE BRAIN-COMPUTER INTERFACE TRAINING USING NEURAL NETWORKS

(71) Applicant: Abby D. Levenberg, New York, NY (US)

(72) Inventor: Abby D. Levenberg, New York, NY (US)

(73) Assignee: TREV LABS, LLC, Dover, DE (US)

( * ) Notice: Subject to any disclaimer, the term of this patent is extended or adjusted under 35 U.S.C. 154(b) by 737 days.

(21) Appl. No.: 16/503,308

(22) Filed: Jul. 3, 2019

(65) Prior Publication Data

US 2021/0005104 A1    Jan. 7, 2021

(51) Int. Cl.
| | |
|---|---|
| *G09B 19/00* | (2006.01) |
| *G06F 3/01* | (2006.01) |
| *G06N 3/04* | (2006.01) |
| *G06N 3/08* | (2006.01) |
| *G06N 3/00* | (2006.01) |
| *A61B 5/369* | (2021.01) |

(52) U.S. Cl.
CPC ............ *G09B 19/003* (2013.01); *A61B 5/369* (2021.01); *G06F 3/015* (2013.01); *G06N 3/006* (2013.01); *G06N 3/04* (2013.01); *G06N 3/08* (2013.01)

(58) Field of Classification Search
CPC ........... G06N 3/049; G06N 3/02; G06N 3/08; G06N 20/00; G06N 3/088; G06N 5/022; G06F 2111/18; G06F 3/0481; G06F 3/04817; G06F 9/4443; G06F 3/04847; G06F 11/3664; G06F 3/012; G06F 3/0304; G06F 3/011–015; G06T 19/00; G06T 17/00; G06T 7/00; G06T 19/006; G06T 2215/16; H04N 5/272; H04N 2201/3245; A63F 13/10; G02B 27/017

See application file for complete search history.

(56) References Cited

U.S. PATENT DOCUMENTS

| | | | | |
|---|---|---|---|---|
| 2014/0315169 | A1* | 10/2014 | Bohbot .................. | G09B 19/00 434/236 |
| 2021/0005104 | A1* | 1/2021 | Levenberg .............. | G06F 3/015 |

FOREIGN PATENT DOCUMENTS

| | | | | |
|---|---|---|---|---|
| WO | WO-2017040417 A1 | * | 3/2017 | ........... A61B 5/0476 |
| WO | WO-2021242927 A1 | * | 12/2021 | |

* cited by examiner

*Primary Examiner* — Todd Buttram
(74) *Attorney, Agent, or Firm* — Galvin Patent Law; Brian R. Galvin; Brian S. Boon

(57) ABSTRACT

A system and method for a multi-stage brain-computer interface training using neural networks that reliably and predictably maps a user's thoughts to particular movements or actions in a computer-generated environment. The system comprises two stages: a pre-training stage, wherein specific exercises are generated on screen, and the brain activity is mapped to the exercises using a neural network as the user attempts to complete the exercises, and an in-use stage, wherein an initial mapping profile is loaded, brain activity is mapped to in-use interactions using a neural network, and those in-use mappings are compared to a library of stored mappings using a neural network to select a more accurate mapping for use in a given situation.

8 Claims, 15 Drawing Sheets

SYSTEM AND METHOD FOR MULTI-STAGE BRAIN-COMPUTER INTERFACE TRAINING USING NEURAL NETWORKS

CROSS-REFERENCE TO RELATED APPLICATIONS

None.

BACKGROUND OF THE INVENTION

Field of the Art

The disclosure relates to the field of brain-computer interfaces, more specifically to the field of training brain-computer interfaces using neural networks and training sets.

Discussion of the State of the Art

In the field of brain-computer interfaces, the key challenge is to accurately map a user's brain activity to actions in a computerized system, whether that system is a videogame, a word processor, a web browser, a flight system, or any other number of tasks for which brain-computer interfaces may be useful. Indeed, the core difficulty of this field is accurately and quickly mapping detected brain activity, such as that from an EEG device, to any digital information which may affect the system in question in a desired way, such as moving an object on screen in a particular direction when the user thinks about moving the object in that direction. Mapping a user's thoughts to particular actions on screen is difficult because of the complexity of the electrical signals produced in the brain, the noisiness of the captured signals, the ambiguity regarding mapping of particular signals or sets of signals to a particular thought, and the differences between individuals in terms of brain activity.

What is needed is a system and method for multi-stage brain-computer interface training that reliably and predictably maps a user's thoughts to particular movements or actions in a computer-generated environment.

SUMMARY OF THE INVENTION

Accordingly, the inventor has conceived, and reduced to practice, a system and method for a multi-stage brain-computer interface training using neural networks that reliably and predictably maps a user's thoughts to particular movements or actions in a computer-generated environment. The system comprises two stages: a training stage, wherein specific exercises are generated on screen, and the electrical signals from the brain are mapped to the exercises using a neural network as the user attempts to complete the exercises, and an in-use stage, wherein an initial mapping profile is loaded, electrical signals from the brain are mapped to in-use interactions using a neural network, and those in-use mappings are compared to a library of stored mappings using a neural network to select a more accurate mapping for use in a given situation. The following non-limiting summary of the invention is provided for clarity, and should be construed consistently with embodiments described in the detailed description below.

According to a preferred embodiment, a system for a multi-stage brain-computer interface training using neural networks is disclosed, comprising: a brain-computer interface manager comprising at least a processor, a memory, and a first plurality of programming instructions stored in the memory and operating on the processor, wherein the programming instructions, when operating on the processor, cause the processor to: receive input from at least one biometric sensor; wherein input from at least one biometric sensor comprises brain-wave or electroencephalographic data from a user; receive configuration profiles from a datastore; send alterations to configuration profiles to a datastore; receive input from a pre-game training engine; wherein input from a pre-game training engine comprises at least alterations to a configuration profile; send output to a pre-game training engine; wherein output sent to a pre-game training engine comprises at least: data from at least one biometric sensor; configuration profile data; and game data; and manage input and output with a computer game; a pre-game training engine comprising at least a processor, a memory, and a second plurality of programming instructions stored in the memory and operating on the processor, wherein the second programming instructions, when operating on the processor, cause the processor to: receive input from a brain-computer interface manager; wherein input from a brain-computer interface manager comprises at least: data from at least one biometric sensor; configuration profile data; and game data; analyze data received from a brain-computer interface manager; analyze data received from a brain-computer interface manager and an executing game; and sending output to a brain-computer interface; wherein output sent to a brain-computer interface comprises at least alterations to a configuration profile.

According to another preferred embodiment, a method for a multi-stage brain-computer interface training using neural networks is disclosed, comprising the steps of: receiving input from at least one biometric sensor, using a brain-computer interface manager; wherein input from at least one biometric sensor comprises brain-wave or electroencephalographic data from a user; receiving configuration profiles from a datastore, using a brain-computer interface manager; sending alterations to configuration profiles to a datastore, using a brain-computer interface manager; receiving input from a pre-game training engine, using a brain-computer interface manager; wherein input from a pre-game training engine comprises at least alterations to a configuration profile; sending output to a pre-game training engine, from a brain-computer interface manager; wherein output sent to a pre-game training engine comprises at least: data from at least one biometric sensor; configuration profile data; and game data; managing input and output with a computer game, using a brain-computer interface manager; receiving input from a brain-computer interface manager, using a pre-game training engine; wherein input from a brain-computer interface manager comprises at least: data from at least one biometric sensor; configuration profile data; and game data; analyzing data received from a brain-computer interface manager, using a pre-game training engine; analyzing data received from a brain-computer interface manager and an executing game, using a pre-game training engine; and sending output to a brain-computer interface, using a pre-game training engine; wherein output sent to a brain-computer interface comprises at least alterations to a configuration profile.

BRIEF DESCRIPTION OF THE DRAWING FIGURES

The accompanying drawings illustrate several aspects and, together with the description, serve to explain the principles of the invention according to the aspects. It will be appreciated by one skilled in the art that the particular arrangements illustrated in the drawings are merely exemplary, and are not to be considered as limiting of the scope of the invention or the claims herein in any way.

DETAILED DESCRIPTION

Figure 1:
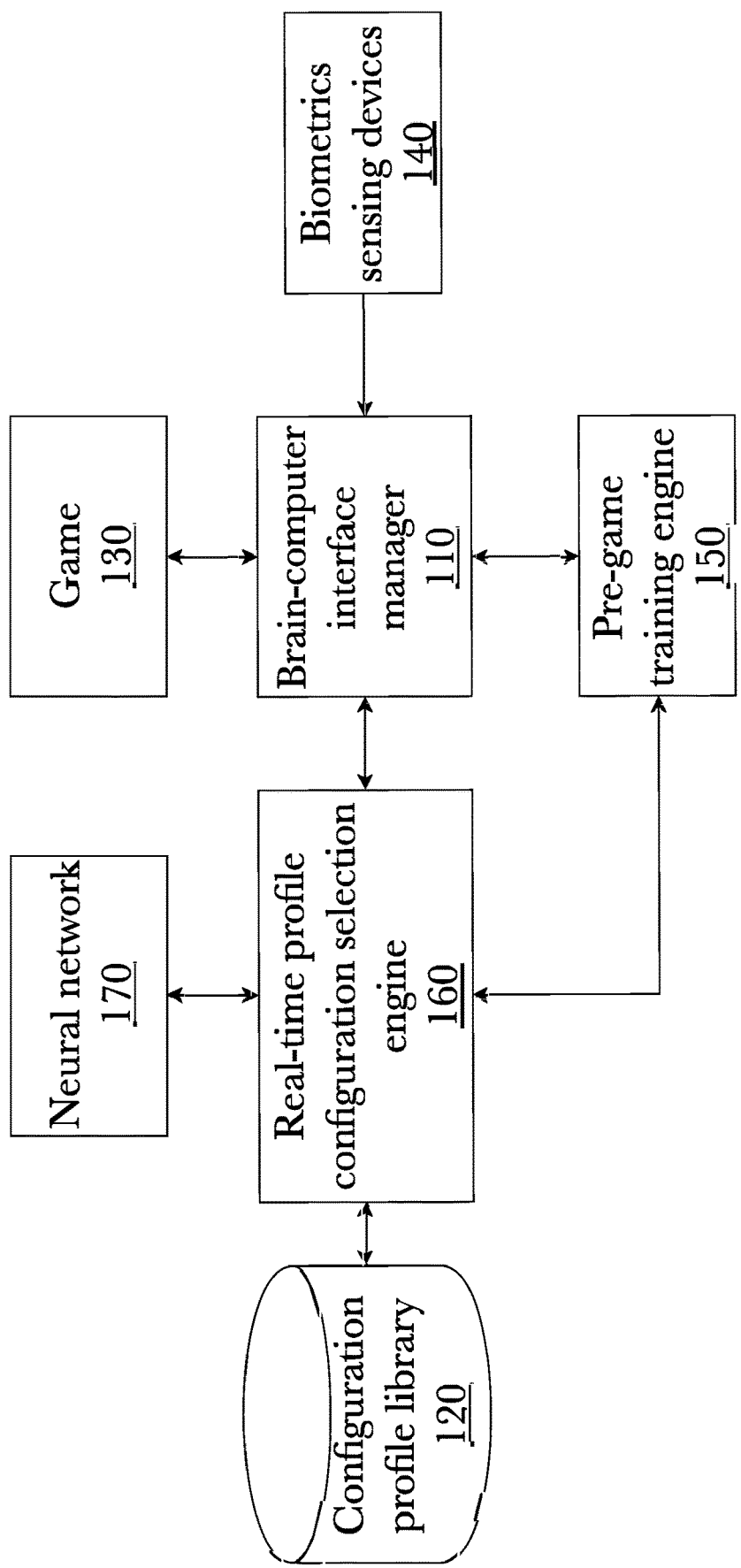
FIG. 1 is a system diagram of components used in a neurogaming system, according to an embodiment.

The inventor has conceived, and reduced to practice, a system and methods for neurogaming using brain-computer interface training.

One or more different aspects may be described in the present application. Further, for one or more of the aspects described herein, numerous alternative arrangements may be described; it should be appreciated that these are presented for illustrative purposes only and are not limiting of the aspects contained herein or the claims presented herein in any way. One or more of the arrangements may be widely applicable to numerous aspects, as may be readily apparent from the disclosure. In general, arrangements are described in sufficient detail to enable those skilled in the art to practice one or more of the aspects, and it should be appreciated that other arrangements may be utilized and that structural, logical, software, electrical and other changes may be made without departing from the scope of the particular aspects. Particular features of one or more of the aspects described herein may be described with reference to one or more particular aspects or figures that form a part of the present disclosure, and in which are shown, by way of illustration, specific arrangements of one or more of the aspects. It should be appreciated, however, that such features are not limited to usage in the one or more particular aspects or figures with reference to which they are described. The present disclosure is neither a literal description of all arrangements of one or more of the aspects nor a listing of features of one or more of the aspects that must be present in all arrangements.

Headings of sections provided in this patent application and the title of this patent application are for convenience only, and are not to be taken as limiting the disclosure in any way.

Devices that are in communication with each other need not be in continuous communication with each other, unless expressly specified otherwise. In addition, devices that are in communication with each other may communicate directly or indirectly through one or more communication means or intermediaries, logical or physical.

A description of an aspect with several components in communication with each other does not imply that all such components are required. To the contrary, a variety of optional components may be described to illustrate a wide variety of possible aspects and in order to more fully illustrate one or more aspects. Similarly, although process steps, method steps, algorithms or the like may be described in a sequential order, such processes, methods and algorithms may generally be configured to work in alternate orders, unless specifically stated to the contrary. In other words, any sequence or order of steps that may be described in this patent application does not, in and of itself, indicate a requirement that the steps be performed in that order. The steps of described processes may be performed in any order practical. Further, some steps may be performed simultaneously despite being described or implied as occurring non-simultaneously (e.g., because one step is described after the other step). Moreover, the illustration of a process by its depiction in a drawing does not imply that the illustrated process is exclusive of other variations and modifications thereto, does not imply that the illustrated process or any of its steps are necessary to one or more of the aspects, and does not imply that the illustrated process is preferred. Also, steps are generally described once per aspect, but this does not mean they must occur once, or that they may only occur once each time a process, method, or algorithm is carried out or executed. Some steps may be omitted in some aspects or some occurrences, or some steps may be executed more than once in a given aspect or occurrence.

When a single device or article is described herein, it will be readily apparent that more than one device or article may be used in place of a single device or article. Similarly, where more than one device or article is described herein, it will be readily apparent that a single device or article may be used in place of the more than one device or article.

The functionality or the features of a device may be alternatively embodied by one or more other devices that are not explicitly described as having such functionality or features. Thus, other aspects need not include the device itself.

Techniques and mechanisms described or referenced herein will sometimes be described in singular form for clarity. However, it should be appreciated that particular aspects may include multiple iterations of a technique or multiple instantiations of a mechanism unless noted otherwise. Process descriptions or blocks in figures should be understood as representing modules, segments, or portions of code which include one or more executable instructions for implementing specific logical functions or steps in the process. Alternate implementations are included within the scope of various aspects in which, for example, functions may be executed out of order from that shown or discussed, including substantially concurrently or in reverse order, depending on the functionality involved, as would be understood by those having ordinary skill in the art.

Definitions

"Artificial intelligence" or "AI" as used herein means a computer system or component that has been programmed in such a way that it mimics some aspect or aspects of cognitive functions that humans associate with human intelligence, such as learning, problem solving, and decision-making. Examples of current AI technologies include understanding human speech, competing successfully in strategic games such as chess and Go, autonomous operation of vehicles, complex simulations, and interpretation of complex data such as images and video.

"Brain-computer interface" or "BCI" as used herein means a device for allowing a user's thoughts to control some aspect of the operation of a computer by detecting the electrical impulses generated by the brain.

"Brain activity," "brainwave," and "brain signal" as used herein each mean electrical activity in the brain as monitored and/or recorded by any technique designed to sense such electrical activity (for example, ECOG, EEG, fMRI, intracortical implants, MEG, etc.

"Biometrics" means any data recorded about a user's body, including, but not limited to brain activity and muscular activity.

"Electrocorticography" or "ECOG" is used in its standard meaning as being an invasive (i.e., requiring surgery) technique for monitoring and/or recording electrical activity in the brain by placing electrodes in direct contact with the brain's surface to measure the electrical activity of the cerebral cortex.

"Electroencephalography" or "EEG" is used in its standard meaning as being a non-invasive technique for monitoring and/or recording electrical activity in the brain through the use of electrodes placed on or near the outside of the scalp.

"Electromyography" or "EMG" is used in its standard meaning as being a minimally-invasive technique for evaluating and recording the electrical activity produced by skeletal muscles.

"Functional magnetic resonance imaging" or "fMRI" is used in its standard meaning as being a non-invasive technique for monitoring and/or recording electrical activity in the brain through the use of magnetic resonance imaging of blood flow in the brain.

"Intracortical implants" is used in its standard meaning as being an invasive (i.e., requiring surgery) technique for monitoring, recording, or stimulating electrical activity in the brain by inserting electrodes into the brain tissue. Implants differ from the other techniques described herein in that they are capable of providing electrical signals to the brain as well as receiving electrical signals from the brain. One current use of intracortical implants a "cochlear implant," which is a prosthetic hearing device that provides a sensation of sound to a person with severe sensorineural hearing loss.

"Machine learning" as used herein is an aspect of artificial intelligence in which the computer system or component can modify its behavior or understanding without being explicitly programmed to do so. Machine learning algorithms develop models of behavior or understanding based on information fed to them as training sets, and can modify those models based on new incoming information.

"Magnetoencephalography" or "MEG" is used in its standard meaning as being a non-invasive neuroimaging technique for mapping brain activity by recording magnetic fields produced by electrical currents occurring naturally in the brain, using very sensitive magnetometers.

"Muscular activity," as used herein means activity in the muscles as monitored and/or recorded by any technique designed to sense such activity (for example, EMG).

"Neural network" as used herein means a computational model, architecture, or system made up of a number of simple, highly interconnected processing elements which process information by their dynamic state response to external inputs, and is thus able to "learn" information by recognizing patterns or trends. Neural networks, also sometimes known as "artificial neural networks" are based on our understanding of the structure and functions of biological neural networks, such as the brains of mammals. A neural network is a framework for application of machine learning algorithms.

Conceptual Architecture

While the invention is by no means limited to particular embodiments or applications described herein, it will be helpful to one of ordinary skill in the art to have examples of embodiments or applications of the system and method described. One embodiment of the invention would be system for neurogaming, wherein a user of the system controls on-screen movements of objects in a computer game by thinking about manipulating those objections. In some aspects, the on-screen objects would be characters or avatars in a 3D open world or virtual reality computer game. Using an embodiment, it is possible to accurately create configuration profiles for users that represent the electrical output of their brains when thinking about controlling the character or avatar, allowing for more accurate and generalized control of the character or avatar.

FIG. 1 is a system diagram of components used in a neurogaming system, according to an embodiment. A brain-computer interface manager 110 is present, as a cyber-physical system that may accept inputs from at least five sources—a real-time profile configuration selection engine 160, a computer game 130, at least one biometric sensing device 140, a pre-game training engine 150, and a configuration profile library 120. Two-way communication is possible between a brain-computer interface manager 110 and at least a real-time profile configuration selection engine 160, a configuration profile library 120, computer game 130, and pre-game training engine 150, and input is accepted from a biometric sensing device 140 into a brain-computer interface manager 110. A real-time profile configuration selection engine 160 also connects to and makes use of a shared neural network 170 with a pre-game training engine 150, the real-time profile configuration selection engine 160 operating for the purposes of selecting and refining user profiles and locating new correlations between user sensory inputs and tasks used for training such as game inputs or outputs, and a user's detected actions through sensor output. A pre-game training engine 150 may receive input from a brain-computer interface manager 110 in the form of at least user biometric sensor data from sensors 140, and be utilized along with data from a configuration profile library 120 to train a new user profile before a game actually begins execution, through either dynamic or pre-determined tasks being performed in a virtual environment, and a user being prompted to either mentally or physically mimic the action, allowing for a baseline training session to establish correlations between game inputs and biometric sensor outputs. A brain-computer interface manager 110 may manage input and output going between the other components communicating with it, such as converting analog signals to digital data, altering or editing input and output to or from the connected components, and filtering the input from the devices into appropriate output for other devices. For example, input from biometrics sensing devices 140 may include EEG information from a user, and based on a pre-game training engine 150 and configuration profile library 120, input from an EEG headset may be translated in the brain-computer interface manager 110 into output sent to a game 130 as input, such as movement in a video game 130. Such EEG input may also be managed by a brain-computer interface manager 110 to send input to a pre-game training engine 150, or send information from a configuration public library 120 to a pre-game training engine 150 and vice versa, as needed. A pre-game training engine 150 may be utilized and configured to create profiles of a user's biometric sensor 140 inputs including possibly EEG inputs, mapping certain biometric output to desired game input, which may then be mapped through a brain-computer interface manager 110. While EEG is used as the primary example of a technique for capturing brain activity data, it is important to note that this is but one example of a variety of techniques that could be used, including, but not limited to, EEG, fMRI, MEG, EMG, and even invasive techniques such as ECOG and intracortical implants.

Figure 2:
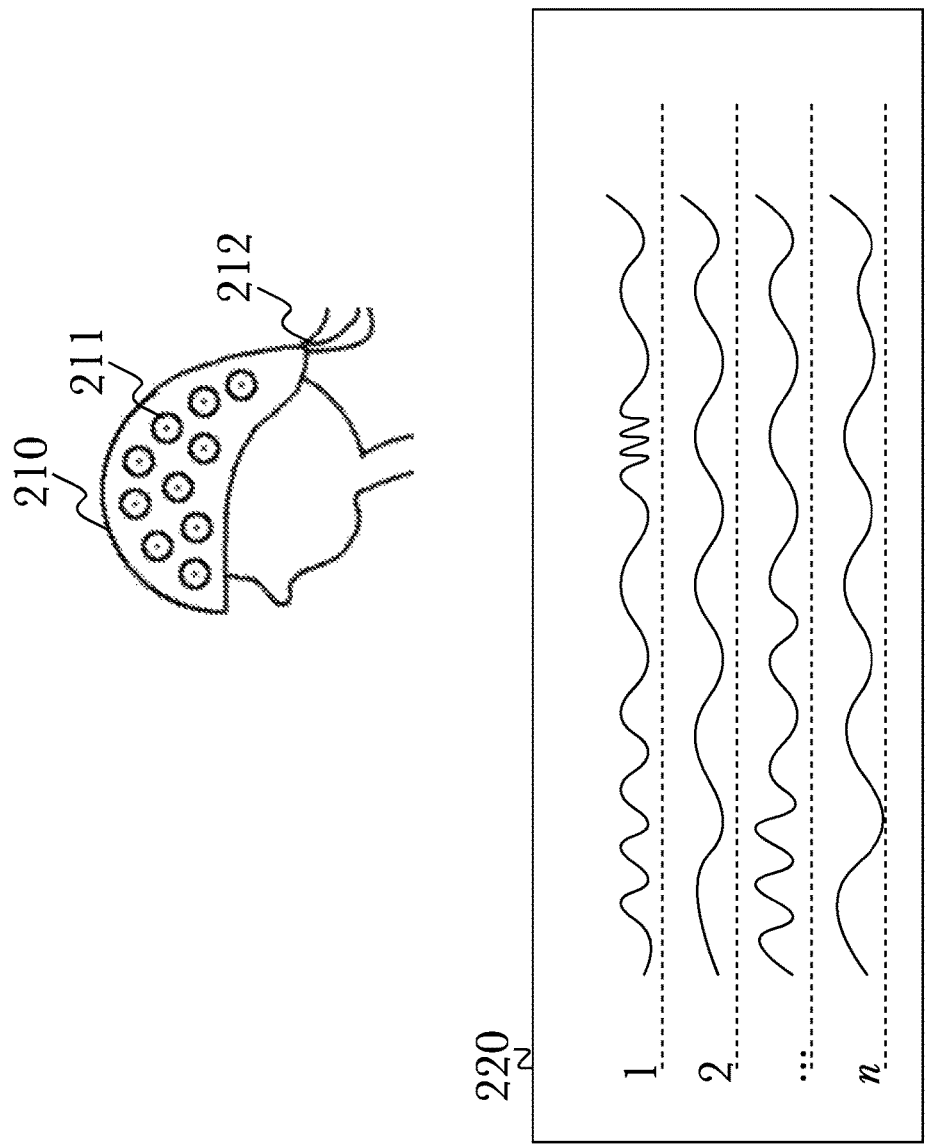
FIG. 2 is a diagram of exemplary EEG headgear with example output from a plurality of electrodes placed near or attached to a user's scalp, according to an aspect of an embodiment.

FIG. 2 is a diagram of exemplary EEG headgear with example output from a plurality of electrodes placed near or attached to a user's scalp, according to an embodiment. An EEG headset 210 may be utilized, comprising at least a set of neuro-sensors 211 for detecting electrical output based on varying brain activities, and a cable or cables extending out of the headset 212 to transmit information from the electrodes 211 to some other device. Such a cable or cables 212 may be a plurality of cables, a ribbon cable, or some other cable type. Shown in the box 220 is an example of EEG output, with signals corresponding to different electrodes numbered from 1 to n. Different electrodes will receive different signals, indicating the electrical signals detected at that point on the user's scalp. This electrical data may be converted to digital signal information by a brain-computer interface manager 110 to produce meaningful input for other devices or components, including a pre-game training engine 150 or a computer game 130.

Figure 3:
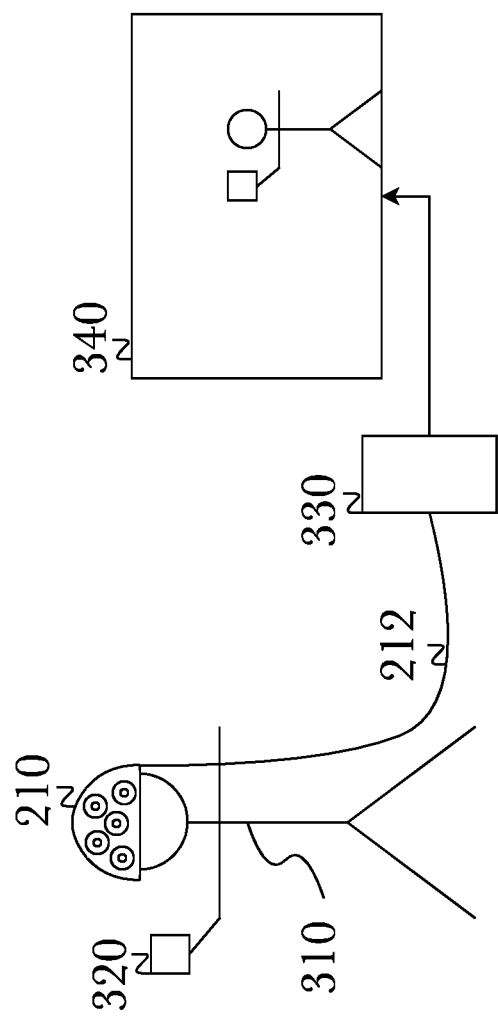
FIG. 3 is a diagram illustrating a human user with appropriate headgear connected to a brain-computer interface and game system, connected to a visual display showing a human avatar performing similar actions to the actual human user.

FIG. 3 is a diagram illustrating a human user with appropriate headgear connected to a brain-computer interface and game system, connected to a visual display showing a human avatar performing similar actions to the actual human user. A human user 310 wears at least an EEG headset 210, and lifts a box object 320, the actual lifting of the box not being as important as the brainwave patterns which may be detected that correspond to the thought of lifting a box. Such biometric sensory data is transmitted through a cable or cables 212 to a device operating a brain-computer interface 330 and some manner of virtual reality ("VR") environment, which is then displayed on a screen 340. The virtual environment display 340 displays a human avatar which performs a similar or identical action to the one actually perceived by the human user 310, in this instance raising and holding a box object.

Figure 4:
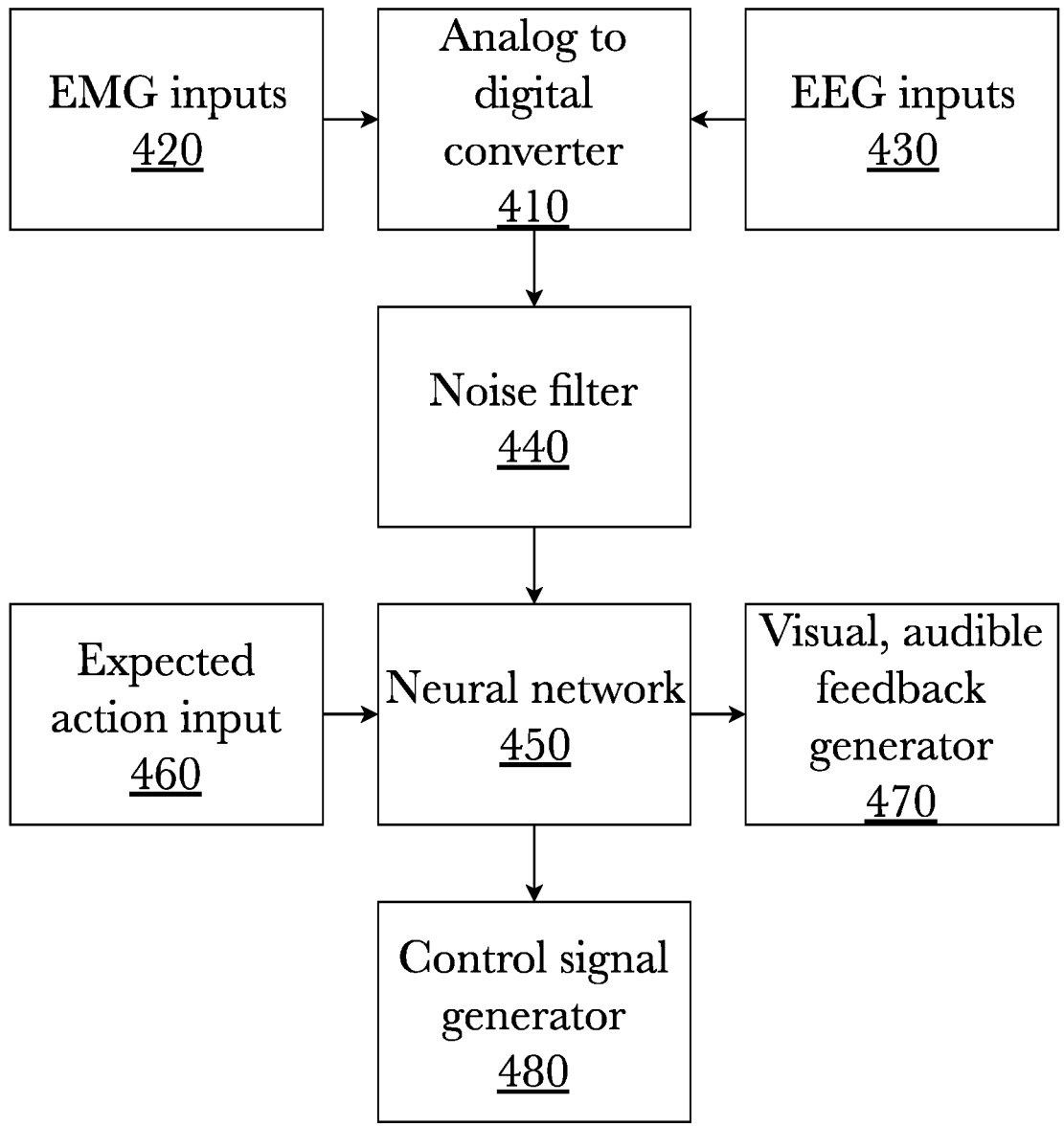
FIG. 4 is flowchart of data and data-handling components used in the operation of a pre-game training analyzer, according to an aspect of an embodiment.

FIG. 4 is flowchart of data and data-handling components used in the operation of a pre-game training analyzer, according to an embodiment. An analog-to-digital converter 410 may accept inputs from biometrics sensors 140 including EMG input 420 and EEG input 430, from stored samples of such data, or from a user interacting with such devices to pre-train the system. Upon receiving such input from either source, the analog signals are converted to digitally represented signal information, before sending the data to a noise filter 440. A noise filter 440 may filter what is determined to be junk or noise data such as minor variations in a physical movement from EMG readings, or minor variance in brain activity patterns from EEG readings, such that only specific variances in the signals and from specific electrodes or sensors may be sent through the noise filter 440 to a neural network 450. A neural network 450 may also be fed an expected action input 460, for example, if a user is meant to move a circle across the screen and into a box also represented on the display, and a specific EEG pattern is consistently output as the user thinks of this task, a neural network 450 may simultaneously learn from the input from a noise filter 440 and expected action 460 to produce visual and audible feedback with a feedback generator 470, showing the task being accomplished on the screen with a human avatar and with any necessary audio feedback, as well as sending the resulting pattern of expected action and sensor input to a control signal generator 480. A control signal generator 480 may actually determine the specific signals associated with the given action, and build a user profile in that manner, as shown in later method diagrams. At the pre-game training stage, a series of generalized pre-defined on-screen tasks is presented to the user. A non-limiting set of examples of pre-defined tasks would be movement of objects from one location to another, resizing of objects, changing the color or objects, changing the shape of objections, etc. While the user attempts to complete the tasks, the system processes the brain activity inputs from the EEG through a neural network 450, which organizes the brain activity inputs into patterns of expected signals for given actions occurring on the screen. Upon completion of the pre-defined tasks, a user profile is generated, mapping brain activity outputs to their corresponding generalized pre-defined tasks. The mappings in the user profile can then be applied to more specific situations. As a non-limiting example, the brain activities mapped to a generalized task of moving a box from the bottom of the screen to the top could be applied to a more specific in-game task of lifting a box.

Figure 5:
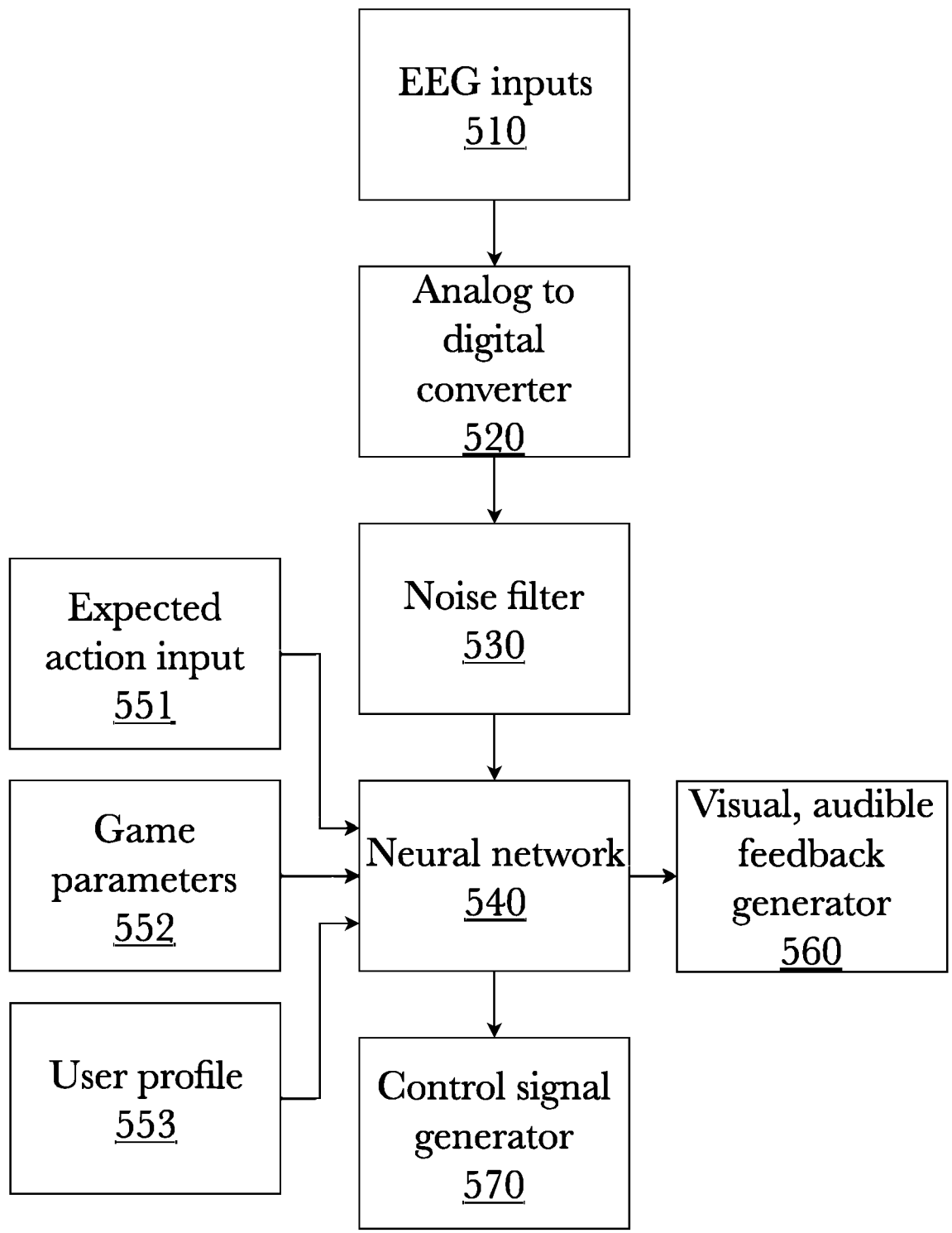
FIG. 5 is a flowchart of data and data-handling components used in the operation of an in-game training analyzer, according to an aspect of an embodiment.

FIG. 5 is a flowchart of data and data-handling components used in the operation of an in-game training analyzer, according to an embodiment. An analog-to-digital converter 520 may accept inputs from biometrics sensors 140 including EEG input 510 from a user interacting with such devices to pre-train the system. Upon receiving such input, the analog signals are converted to digitally represented signal information, before sending the data to a noise filter 530. A noise filter 530 may filter what is determined to be junk or noise data such as minor variance in brain activity patterns from EEG readings, such that only specific variances in the signals and from specific electrodes or sensors may be sent through the noise filter 530 to a neural network 540. A neural network 550 may also be fed expected action input 551, for example, if a user is meant to move a circle across the screen and into a box also represented on the display, and a specific EEG pattern is consistently output as the user thinks of this task, a neural network 540 may simultaneously learn from the input from a noise filter 530 and expected action 551, as well as the game parameters 552 and user profile 553, the user profile being in part determined by the pre-game training analyzer 330 operations, to produce visual and audible feedback with a feedback generator 560. Output from a neural network 540 may include showing the task being accomplished on the screen and with any necessary audio feedback, as well as sending the resulting pattern of expected action and sensor input to a control signal generator 570. A control signal generator 570 may determine the specific signals associated with the given action, and build a user profile in that manner, as shown in later method diagrams. During game play, a neural network will constantly monitor the brain activity in relation to expected brain activity relative to the activities on screen, and will compare that brain activity to profiles in a library to select an the most accurate and responsive brain activity profile for a given set of parameters. The parameters for which a profile may be selected from the library may include any parameters relevant to optimization of the brain-computer interface, such as a user's pre-game training profiles, a user's past brain activity related to a particular game or activity, the type of game being played, a particular sequence of movements or activity on the screen, etc.

Figure 6:
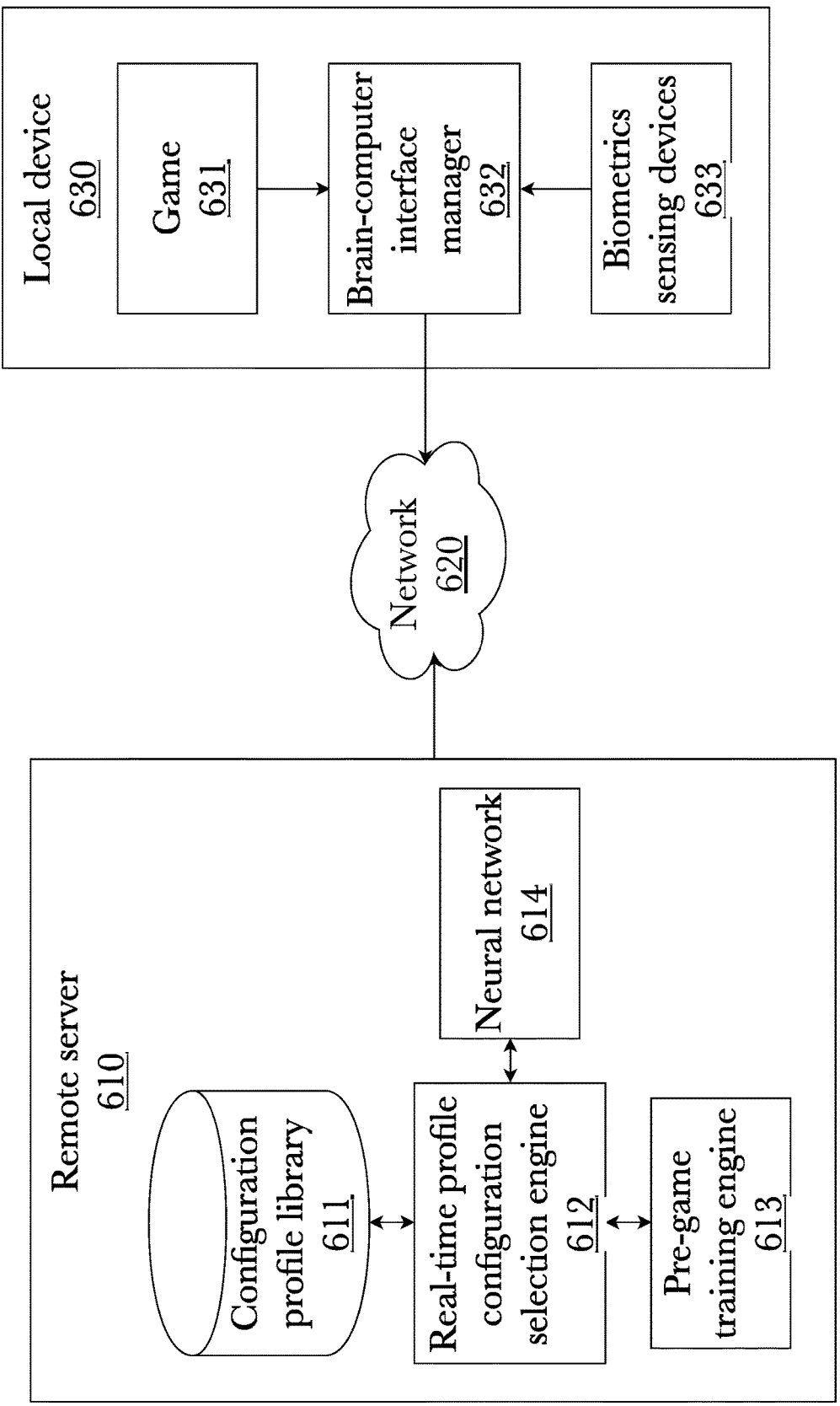
FIG. 6 is a system diagram of an alternative embodiment of a neurogaming training system, showing the components in a neurogaming system distributed across a remote server and local device, connected by a network.

FIG. 6 is a system diagram of an alternative embodiment of a neurogaming training system, showing the components in a neurogaming system distributed across a remote server and local device, connected by a network. According to this embodiment, a configuration profile library 611, real-time profile configuration selection engine 612 and an accompanying neural network 614, and a pre-game training engine 613 are located on a remote server 610. A real-time profile configuration selection engine 612 and pre-game training engine 613 may both utilize a neural network 614, as well as utilizing a connection to a configuration profile library 611 for the purposes of both selecting and refining a user profile before and during gameplay. A remote server 610 may respond to queries from across a network 620, to correlate biometric sensor data with stored user profiles in a configuration profile library 611 using a pre-game training engine 613 before game execution or using a real-time profile selection engine 612 during gameplay to utilize the closest biometric profile to a user's sensor outputs, for the purpose of finding a configuration of sensor input correlated with game input that most closely matches a user's sensory output compared to a training environment's output. Across a network 620, a computer game 631, brain computer interface manager 632, and one or more biometrics sensing devices 633 are located separately from a remote server 610 on a local device 630. A pre-game training engine 613, profile selection engine 612 and accompanying neural network 614, and configuration profile library 611, may be connected on the same server together, and the server's connection over a network 620 to a local device 630 hosting a brain-computer interface 632, a game 631, and at least a singular biometric sensing device 633, allows for essentially all components to communicate bi-directionally with each other through the intermediary brain-computer interface manager 632. The local device 630 and remote server 610 are connected over a network 620 for communication, such a network possibly being the Internet, an intranet, or some other local area or wide area network, as is common in the art. A brain-computer interface manager 632 is present, as a cyber-physical system that may accept inputs from multiple sources—a configuration profile library 611, a game 631, at least one biometric sensing device 633, and a pre-game training engine 613. Two-way communication is possible between a brain-computer interface 632 and at least a configuration profile selection engine 612, computer game 631, and pre-game training engine 613, while only input is accepted from a biometric sensing device or devices 633 into a brain-computer interface manager 632. A brain-computer interface manager 632 may manage input and output going between the other components communicating with it, such as converting analog signals to digital data, altering or editing input and output to or from the connected components, and filtering the input from the devices into appropriate output for other devices. For example, input from biometrics sensing devices 633 may include EEG information from a user, and based on a pre-game training engine 613 and configuration profile library 611, input from an EEG headset may be translated in the brain-computer interface manager 632 into output sent to a game 631 as input, such as movement in a video game 631, utilizing mapped biometric sensory data as input instead of another common input method such as a joystick. Such EEG input may also be managed by a brain-computer interface manager to send input to a pre-game training engine 613, or send information from a configuration public library 611 to a pre-game training engine 613 and vice versa, as needed. A pre-game training engine 613 may be utilized and configured to create profiles of a user's biometric sensor 633 inputs including possibly EEG inputs, mapping certain biometric output to desired game input, which may then be mapped through a brain-computer interface manager 632.

Figure 7:
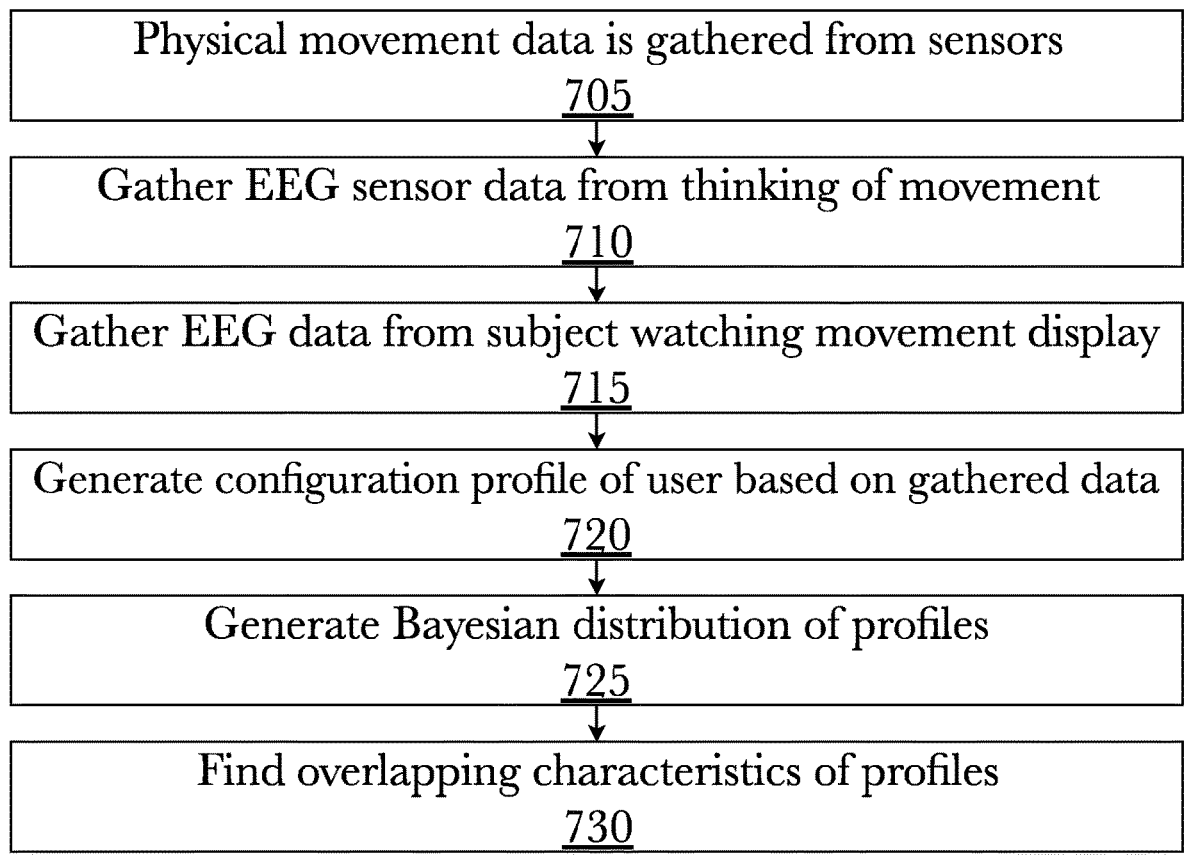
FIG. 7 is a method diagram illustrating the function of a pre-game training analyzer in a neurogaming system, according to an embodiment.

FIG. 7 is a method diagram illustrating the function of a pre-game training analyzer in a neurogaming system, according to an embodiment. Physical movement data is received from sensors such as EMG sensors 705 to determine user movement in relation to desired tasks, which may be applicable for certain types of training. A user may be requested on-screen to think of a certain movement, at which point EEG sensor data may be gathered 710, while a user is then asked to watch a similar movement on the display 715. The combination of having a user think of the same movement as what appears on the screen allows for relational learning by a neural network between EEG output and screen output, and allows for a user profile to be generated 720 based on the patterns of EEG and visual data output recorded. A Bayesian distribution of profiles is re-computed 725 with the new user profile data, to find overlapping characteristics and patterns in profiles 730, which may allow for future developments such as pre-loaded generalized patterns for new users, or some other purpose.

Figure 8:
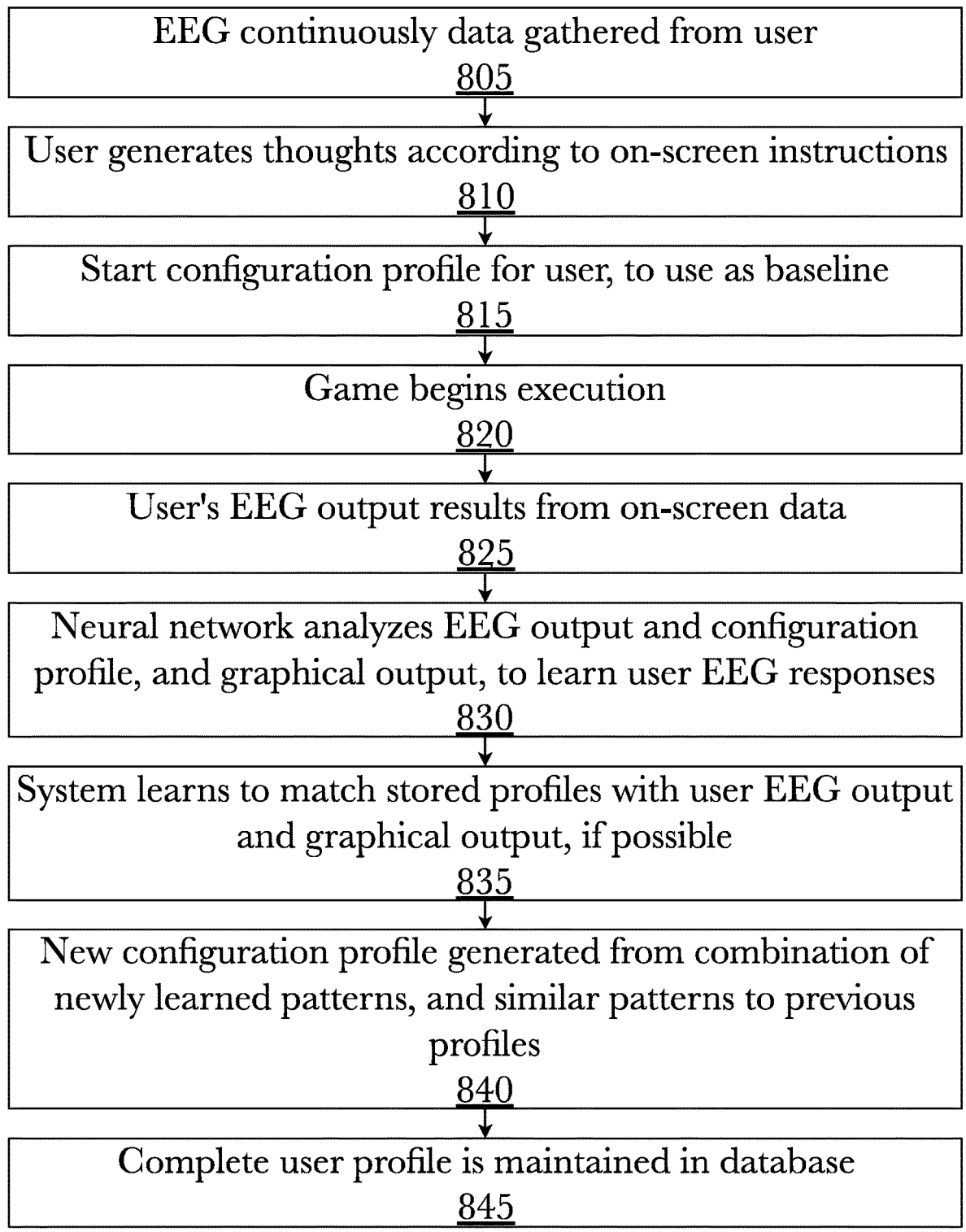
FIG. 8 is a method diagram illustrating the function of an in-game training analyzer in a neurogaming system, according to an aspect of an embodiment.

FIG. 8 is a method diagram illustrating the function of an in-game training analyzer in a neurogaming system, according to an embodiment. As an in-game training method, the system receives EEG input from a user 805, continuously so long as the equipment is worn and maintains proper functionality. EEG data will reflect a user's brain activity as responses to on-screen instructions 810, such as needing to move an object on the screen, or some other task. As this is done, a baseline configuration is initialized 815 comprising at least the pre-game training profile accomplished in FIG. 7, before the game begins execution 820. During game execution, a user's EEG output is processed as resulting from on-screen data and in-game data 825, allowing the in-game training analyzer 310 to communicate with a neural network 320 and analyze a user's EEG output, configuration profile, and the output of the game execution, to associate patterns of user EEG responses with corresponding game responses 830. Using the previous Bayesian distribution of profiles to find common characteristics 725, 730, the system may use a neural network 320, 540 to find configuration profiles which match the desired action to the user's EEG output 835, in order to utilize previously learned patterns in the event that a user has similar EEG readings to a profile in the library for a given user, game, or activity. A new configuration profile may be generated using the gathered pattern data 840, or the system may alter the currently accessed profile, before storing the user configuration profile in a database or configuration profile library 845.

Figure 9:
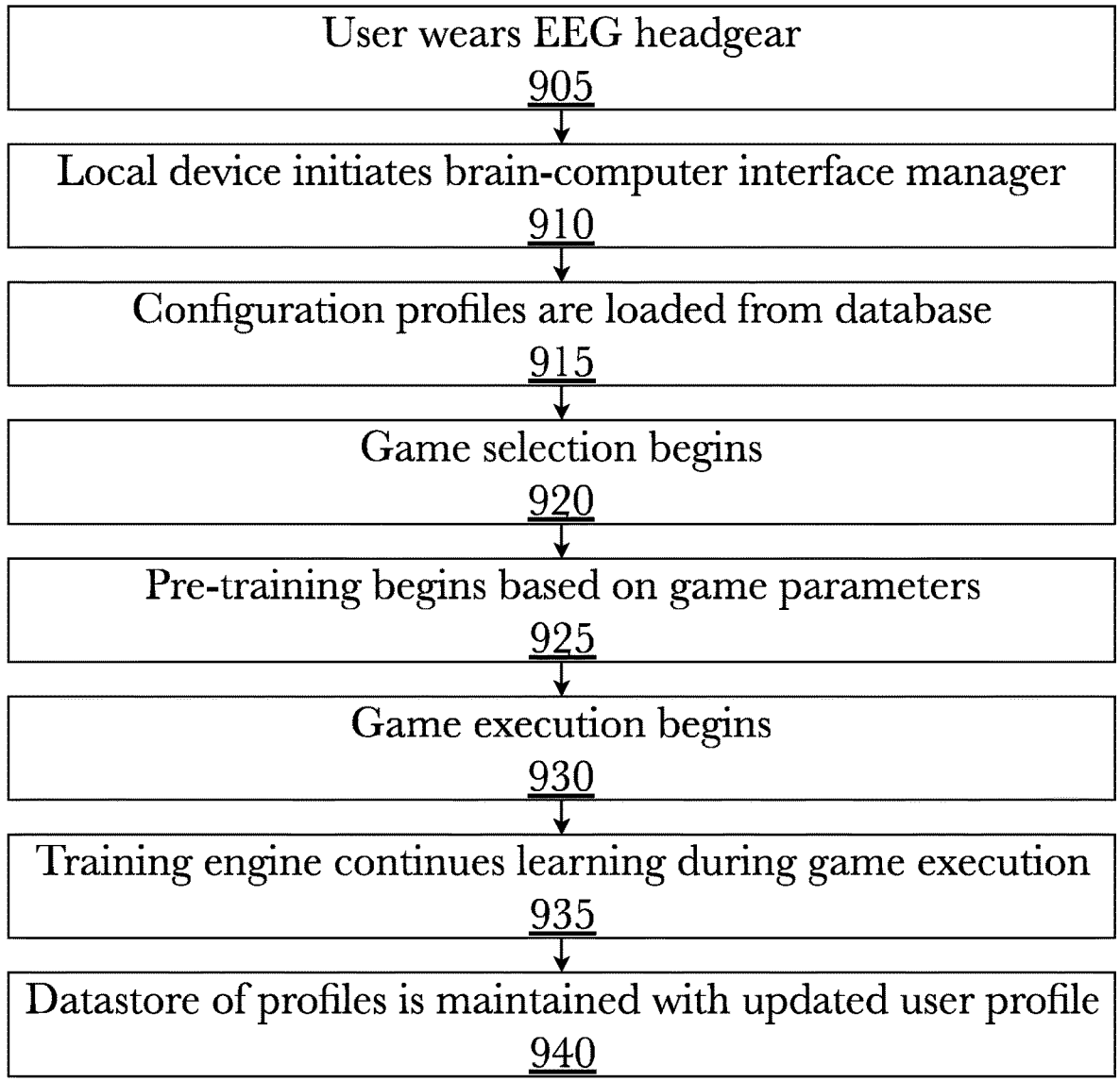
FIG. 9 is a method diagram illustrating the overall function of a neurogaming system, according to an embodiment.

FIG. 9 is a method diagram illustrating the overall function of a neurogaming system, according to an embodiment. A user first wears EEG headgear 905, before a local device initiates operation of a brain-computer interface manager 910. One the manager is initiated, other components may be connected and initiated, before configuration profiles are loaded from a datastore 915. Once configuration profiles are loaded 915, a game selection screen may be initiated 920, allowing for pre-game training which may take into account the parameters of the selected game 925. Once game execution begins 930 after pre-game training 925, training may continue during game execution 935 as described in FIG. 8, with a configuration profile library or datastore being maintained with updates to user configuration profiles 940 as required.

Figure 14:
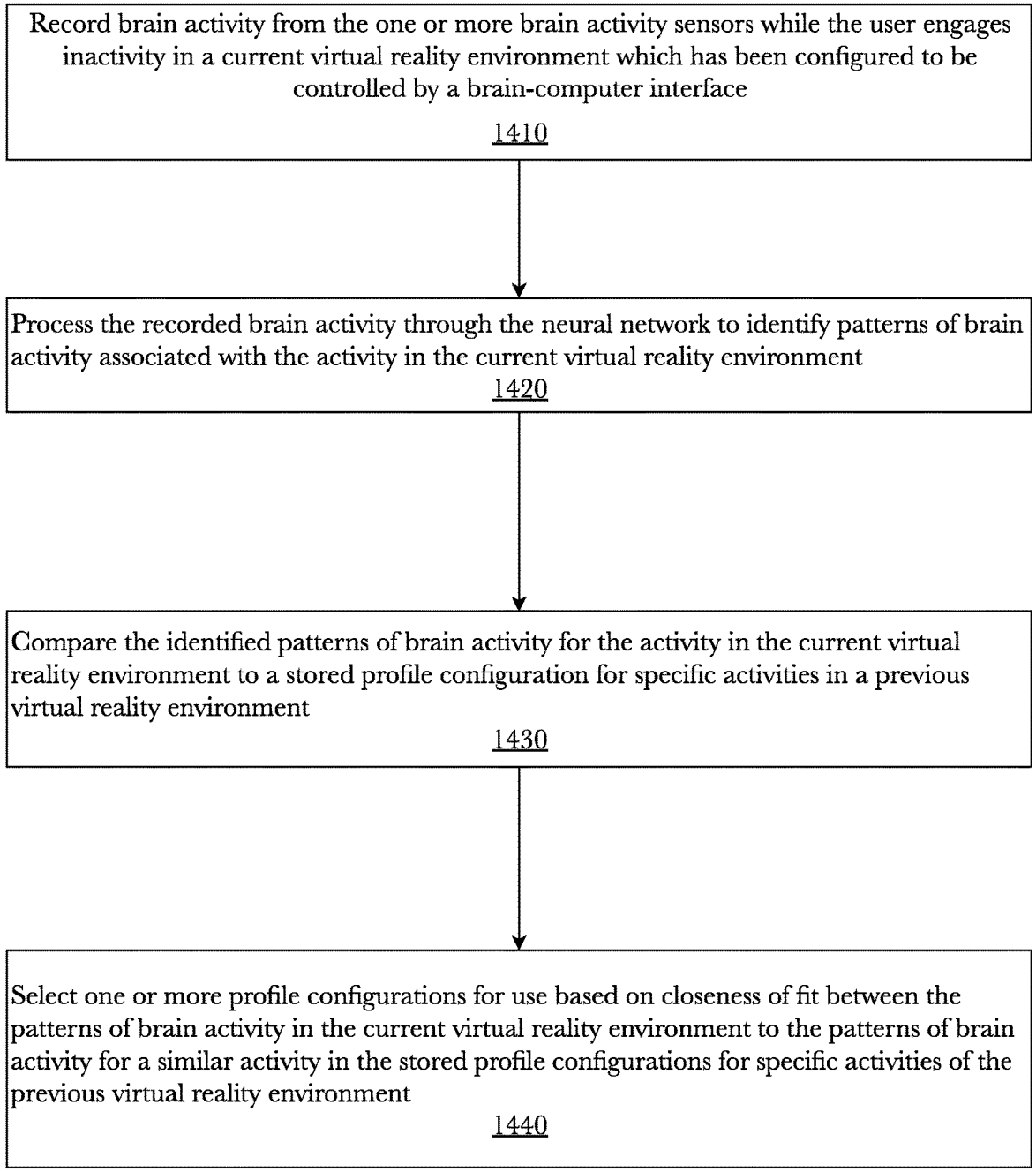
FIG. 14 is a method diagram illustrating the operation of a real-time profile configuration engine, and the selection of a configuration profile from a library based on correlated user sensor data and computer-controlled game output.

FIG. 14 is a method diagram illustrating the operation of a real-time profile configuration engine, and the selection of a configuration profile from a library based on correlated user sensor data and computer-controlled game output. First the system may record brain activity from the one or more brain activity sensors 1410 while the user engages in activity in a current virtual reality environment which has been configured to be controlled by a brain computer interface.

The system the processes the recorded brain activity through the neural network to identify patterns of brain activity associated with the activity in the current virtual reality environment 1420. Identified patterns of brain activity for the activity in the current virtual reality environment are compared to a stored profile configuration for specific activities in a previous virtual reality environment 1430, and a profile configuration is selected for use based on closeness of fit between the patterns of brain activity in the current virtual reality environment to the patterns of brain activity for a similar activity in the stored profile configurations for specific activities of the previous virtual reality environment 1440. It should be noted that the profile configurations created by the pre-game training engine could be used by the real-time profile configuration selection engine either with the same user or with a different user.

Figure 15:
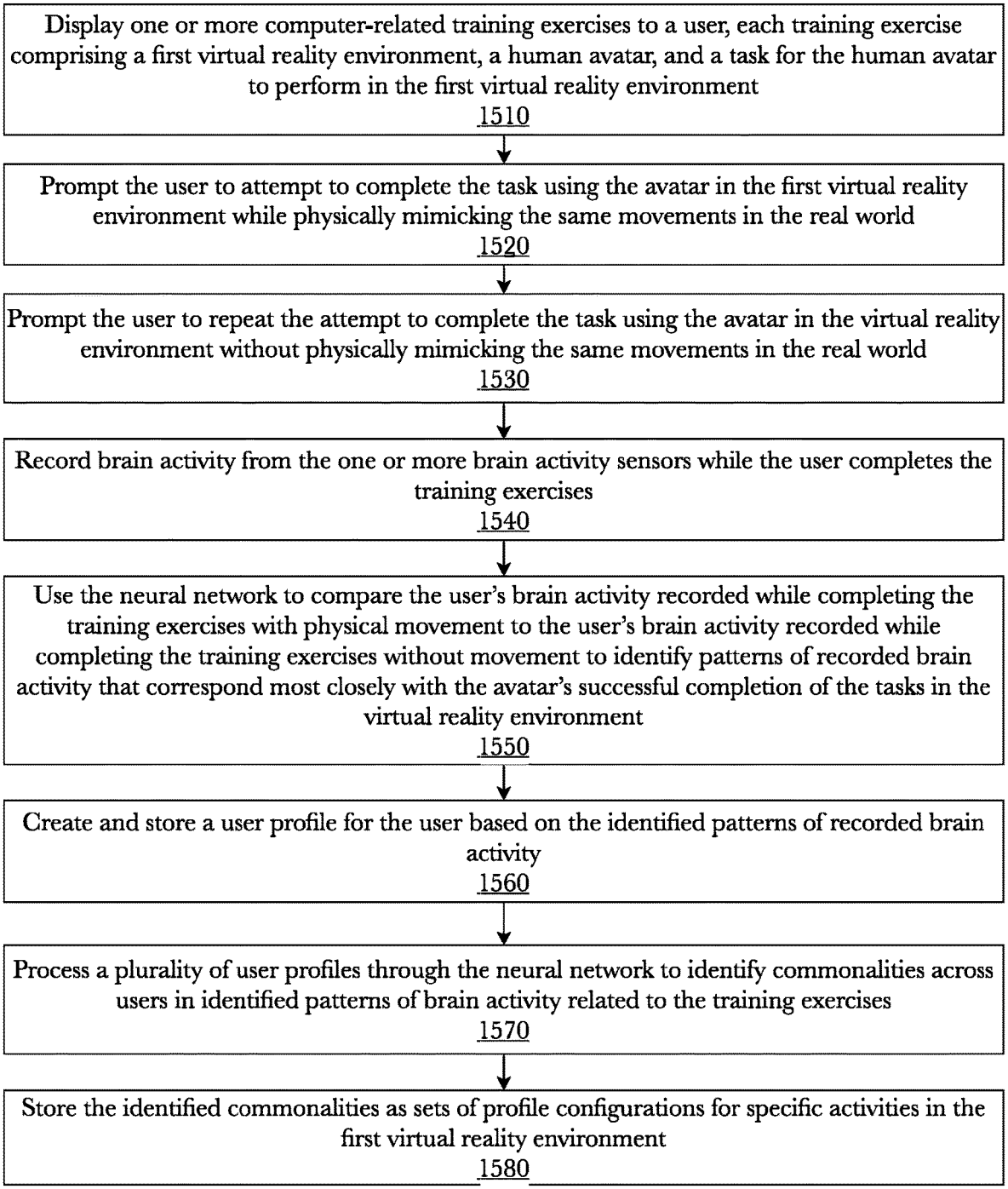
FIG. 15 is a method diagram illustrating the functionality of a pre-game training engine to train a neural network to train a user profile to match a user's brain activity during certain mental activities and map them to possible game inputs.

FIG. 15 is a method diagram illustrating the functionality of a pre-game training engine to use a neural network to train a user profile to match a user's brain activity during certain mental activities and map them to possible game inputs. First, a virtual reality headset or other display may display one or more computer-related training exercises to a user, each training exercise comprising a first virtual reality environment, a human avatar, and a task for the human avatar to perform in the first virtual reality environment 1510, allowing a user to visually view the exercises or motions. The pre-game training engine may then prompt the user to attempt to complete the task using the avatar in the first virtual reality environment while physically mimicking the same movements in the real world 1520, for example a user may be prompted to pick up an actual physical box in front of them at the same time as the human avatar in the virtual reality environment automatically does so. The user may be prompted to repeat the attempt to complete the task using the avatar in the virtual reality environment without physically mimicking the same movements in the real world 1530, for instance by merely thinking similar thoughts but without physically performing the task, so that the training engine may record brain activity from the one or more brain activity sensors while the user completes the training exercises 1540 and use a neural network to compare the user's brain activity recorded while completing the training exercises with physical movement to the user's brain activity recorded while completing the training exercises without movement, to identify patterns of recorded brain activity that correspond most closely with the avatar's successful completion of the tasks in the virtual reality environment 1550. After this is accomplished and correlations are sufficiently strong as may be dictated by system configuration settings, the pre-game training engine may create and store a user profile for the user based on the identified patterns of recorded brain activity 1560, for the purpose of recording the data for future use rather than requiring pre-game training every time a user may wish to utilize the system to execute a virtual reality simulation or game. Lastly, the training engine will process a plurality of user profiles with a neural network to identify commonalities across users in identified patterns of brain activity related to the training exercises 1570 and store the identified commonalities as sets of profile configurations for specific activities in the first virtual reality environment 1580 with a configuration profile library, so that commonalities between users' sensor data may result in finding more precise ways to process sensor input into game input. Potentially, with enough user configuration profiles stored and enough correlations between virtual reality inputs and biometric sensor outputs, a user may only need to spend a few minutes at most in a pre-game training session on first using the system, for it to select a user profile configuration or configurations that closely match the user's biometric feedback, resulting in quick configuration and allowing a user to then interact with a virtual environment quickly and accurately.

Hardware Architecture

Generally, the techniques disclosed herein may be implemented on hardware or a combination of software and hardware. For example, they may be implemented in an operating system kernel, in a separate user process, in a library package bound into network applications, on a specially constructed machine, on an application-specific integrated circuit ("ASIC"), or on a network interface card.

Software/hardware hybrid implementations of at least some of the aspects disclosed herein may be implemented on a programmable network-resident machine (which should be understood to include intermittently connected network-aware machines) selectively activated or reconfigured by a computer program stored in memory. Such network devices may have multiple network interfaces that may be configured or designed to utilize different types of network communication protocols. A general architecture for some of these machines may be described herein in order to illustrate one or more exemplary means by which a given unit of functionality may be implemented. According to specific aspects, at least some of the features or functionalities of the various aspects disclosed herein may be implemented on one or more general-purpose computers associated with one or more networks, such as for example an end-user computer system, a client computer, a network server or other server system, a mobile computing device (e.g., tablet computing device, mobile phone, smartphone, laptop, or other appropriate computing device), a consumer electronic device, a music player, or any other suitable electronic device, router, switch, or other suitable device, or any combination thereof. In at least some aspects, at least some of the features or functionalities of the various aspects disclosed herein may be implemented in one or more virtualized computing environments (e.g., network computing clouds, virtual machines hosted on one or more physical computing machines, or other appropriate virtual environments).

Figure 10:
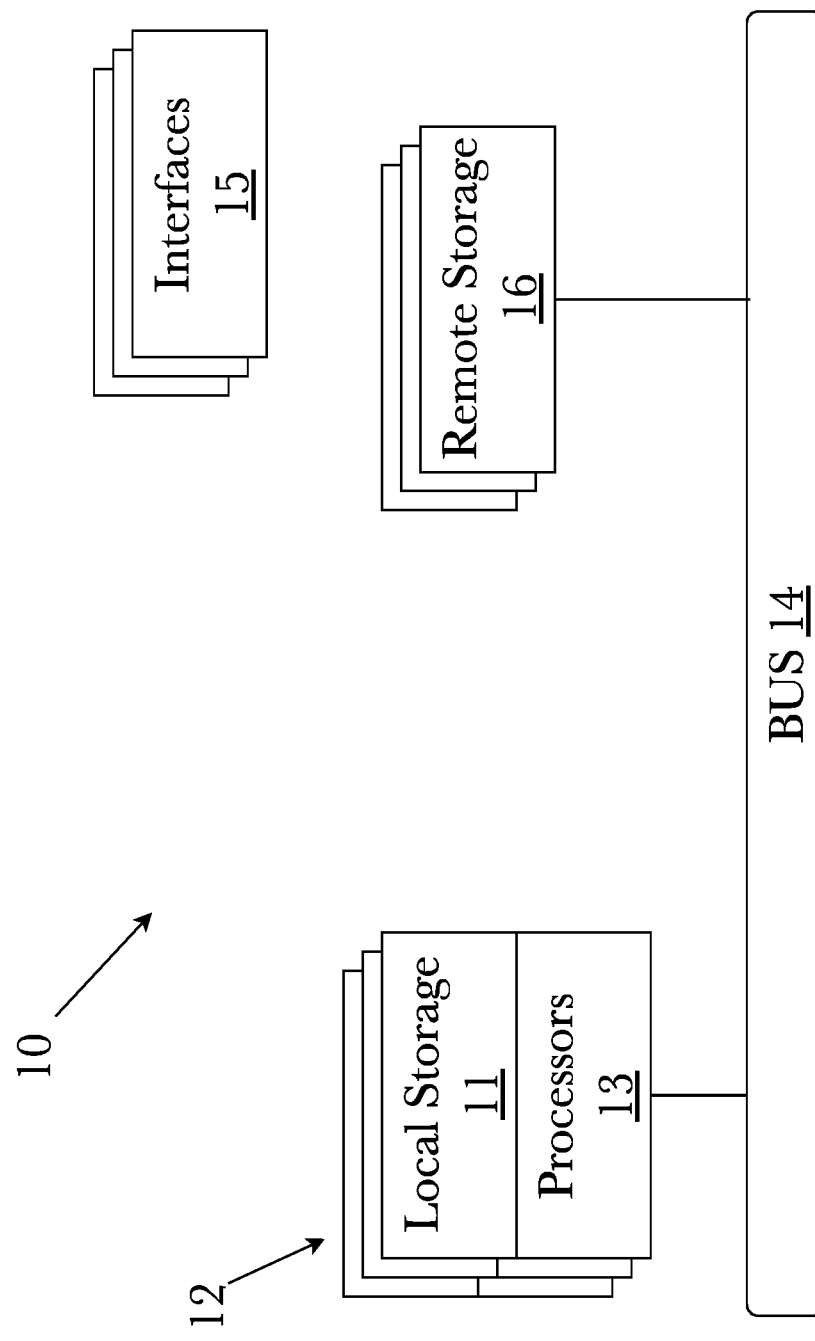
FIG. 10 is a block diagram illustrating an exemplary hardware architecture of a computing device.

Referring now to FIG. 10, there is shown a block diagram depicting an exemplary computing device 10 suitable for implementing at least a portion of the features or functionalities disclosed herein. Computing device 10 may be, for example, any one of the computing machines listed in the previous paragraph, or indeed any other electronic device capable of executing software- or hardware-based instructions according to one or more programs stored in memory. Computing device 10 may be configured to communicate with a plurality of other computing devices, such as clients or servers, over communications networks such as a wide area network a metropolitan area network, a local area network, a wireless network, the Internet, or any other network, using known protocols for such communication, whether wireless or wired.

In one aspect, computing device 10 includes one or more central processing units (CPU) 12, one or more interfaces 15, and one or more busses 14 (such as a peripheral component interconnect (PCI) bus). When acting under the control of appropriate software or firmware, CPU 12 may be responsible for implementing specific functions associated with the functions of a specifically configured computing device or machine. For example, in at least one aspect, a computing device 10 may be configured or designed to function as a server system utilizing CPU 12, local memory 11 and/or remote memory 16, and interface(s) 15. In at least one aspect, CPU 12 may be caused to perform one or more of the different types of functions and/or operations under the control of software modules or components, which for example, may include an operating system and any appropriate applications software, drivers, and the like.

CPU 12 may include one or more processors 13 such as, for example, a processor from one of the Intel, ARM, Qualcomm, and AMD families of microprocessors. In some aspects, processors 13 may include specially designed hardware such as application-specific integrated circuits (ASICs), electrically erasable programmable read-only memories (EEPROMs), field-programmable gate arrays (FPGAs), and so forth, for controlling operations of computing device 10. In a particular aspect, a local memory 11 (such as non-volatile random access memory (RAM) and/or read-only memory (ROM), including for example one or more levels of cached memory) may also form part of CPU 12. However, there are many different ways in which memory may be coupled to system 10. Memory 11 may be used for a variety of purposes such as, for example, caching and/or storing data, programming instructions, and the like. It should be further appreciated that CPU 12 may be one of a variety of system-on-a-chip (SOC) type hardware that may include additional hardware such as memory or graphics processing chips, such as a QUALCOMM SNAPDRAGON™ or SAMSUNG EXYNOS™ CPU as are becoming increasingly common in the art, such as for use in mobile devices or integrated devices.

As used herein, the term "processor" is not limited merely to those integrated circuits referred to in the art as a processor, a mobile processor, or a microprocessor, but broadly refers to a microcontroller, a microcomputer, a programmable logic controller, an application-specific integrated circuit, and any other programmable circuit.

In one aspect, interfaces 15 are provided as network interface cards (NICs). Generally, NICs control the sending and receiving of data packets over a computer network; other types of interfaces 15 may for example support other peripherals used with computing device 10. Among the interfaces that may be provided are Ethernet interfaces, frame relay interfaces, cable interfaces, DSL interfaces, token ring interfaces, graphics interfaces, and the like. In addition, various types of interfaces may be provided such as, for example, universal serial bus (USB), Serial, Ethernet, FIREWIRE™, THUNDERBOLTIm, PCI, parallel, radio frequency (RF), BLUETOOTH™, near-field communications (e.g., using near-field magnetics), 802.11 (WiFi), frame relay, TCP/IP, ISDN, fast Ethernet interfaces, Gigabit Ethernet interfaces, Serial ATA (SATA) or external SATA (ESATA) interfaces, high-definition multimedia interface (HDMI), digital visual interface (DVI), analog or digital audio interfaces, asynchronous transfer mode (ATM) interfaces, high-speed serial interface (HSSI) interfaces, Point of Sale (POS) interfaces, fiber data distributed interfaces (FDDIs), and the like. Generally, such interfaces 15 may include physical ports appropriate for communication with appropriate media. In some cases, they may also include an independent processor (such as a dedicated audio or video processor, as is common in the art for high-fidelity AN hardware interfaces) and, in some instances, volatile and/or non-volatile memory (e.g., RAM).

Although the system shown in FIG. 10 illustrates one specific architecture for a computing device 10 for implementing one or more of the aspects described herein, it is by no means the only device architecture on which at least a portion of the features and techniques described herein may be implemented. For example, architectures having one or any number of processors 13 may be used, and such processors 13 may be present in a single device or distributed among any number of devices. In one aspect, a single processor 13 handles communications as well as routing computations, while in other aspects a separate dedicated communications processor may be provided. In various aspects, different types of features or functionalities may be implemented in a system according to the aspect that includes a client device (such as a tablet device or smartphone running client software) and server systems (such as a server system described in more detail below).

Regardless of network device configuration, the system of an aspect may employ one or more memories or memory modules (such as, for example, remote memory block 16 and local memory 11) configured to store data, program instructions for the general-purpose network operations, or other information relating to the functionality of the aspects described herein (or any combinations of the above). Program instructions may control execution of or comprise an operating system and/or one or more applications, for example. Memory 16 or memories 11, 16 may also be configured to store data structures, configuration data, encryption data, historical system operations information, or any other specific or generic non-program information described herein.

Because such information and program instructions may be employed to implement one or more systems or methods described herein, at least some network device aspects may include nontransitory machine-readable storage media, which, for example, may be configured or designed to store program instructions, state information, and the like for performing various operations described herein. Examples of such nontransitory machine-readable storage media include, but are not limited to, magnetic media such as hard disks, floppy disks, and magnetic tape; optical media such as CD-ROM disks; magneto-optical media such as optical disks, and hardware devices that are specially configured to store and perform program instructions, such as read-only memory devices (ROM), flash memory (as is common in mobile devices and integrated systems), solid state drives (SSD) and "hybrid SSD" storage drives that may combine physical components of solid state and hard disk drives in a single hardware device (as are becoming increasingly common in the art with regard to personal computers), memristor memory, random access memory (RAM), and the like. It should be appreciated that such storage means may be integral and non-removable (such as RAM hardware modules that may be soldered onto a motherboard or otherwise integrated into an electronic device), or they may be removable such as swappable flash memory modules (such as "thumb drives" or other removable media designed for rapidly exchanging physical storage devices), "hot-swappable" hard disk drives or solid state drives, removable optical storage discs, or other such removable media, and that such integral and removable storage media may be utilized interchangeably. Examples of program instructions include both object code, such as may be produced by a compiler, machine code, such as may be produced by an assembler or a linker, byte code, such as may be generated by for example a JAVA™ compiler and may be executed using a Java virtual machine or equivalent, or files containing higher level code that may be executed by the computer using an interpreter (for example, scripts written in Python, Perl, Ruby, Groovy, or any other scripting language).

Figure 11:
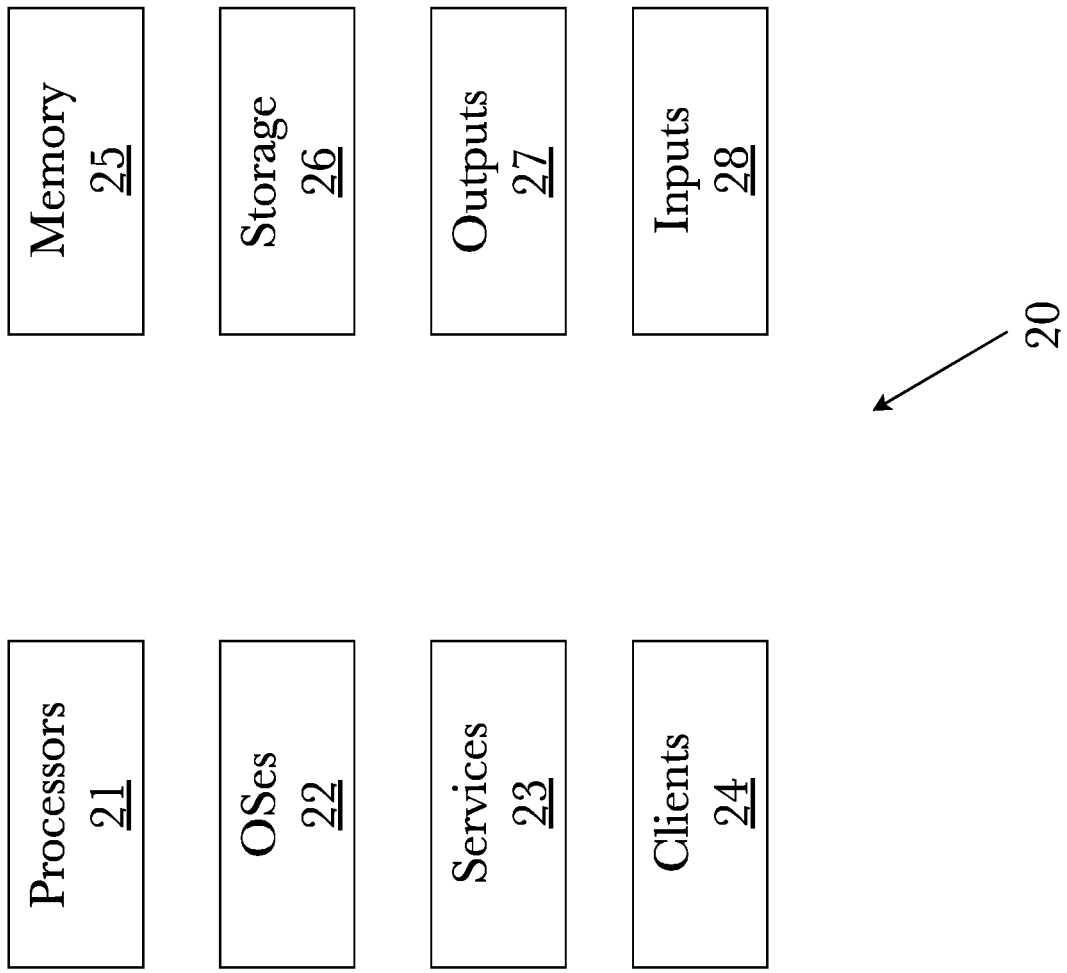
FIG. 11 is a block diagram illustrating an exemplary logical architecture for a client device.

In some aspects, systems may be implemented on a standalone computing system. Referring now to FIG. 11, there is shown a block diagram depicting a typical exemplary architecture of one or more aspects or components thereof on a standalone computing system. Computing device 20 includes processors 21 that may run software that carry out one or more functions or applications of aspects, such as for example a client application 24. Processors 21 may carry out computing instructions under control of an operating system 22 such as, for example, a version of MICROSOFT WINDOWS™ operating system, APPLE macOS™ or iOS™ operating systems, some variety of the Linux operating system, ANDROID™ operating system, or the like. In many cases, one or more shared services 23 may be operable in system 20, and may be useful for providing common services to client applications 24. Services 23 may for example be WINDOWS™ services, user-space common services in a Linux environment, or any other type of common service architecture used with operating system 21. Input devices 28 may be of any type suitable for receiving user input, including for example a keyboard, touchscreen, microphone (for example, for voice input), mouse, touchpad, trackball, or any combination thereof. Output devices 27 may be of any type suitable for providing output to one or more users, whether remote or local to system 20, and may include for example one or more screens for visual output, speakers, printers, or any combination thereof. Memory 25 may be random-access memory having any structure and architecture known in the art, for use by processors 21, for example to run software. Storage devices 26 may be any magnetic, optical, mechanical, memristor, or electrical storage device for storage of data in digital form (such as those described above, referring to FIG. 10). Examples of storage devices 26 include flash memory, magnetic hard drive, CD-ROM, and/or the like.

Figure 12:
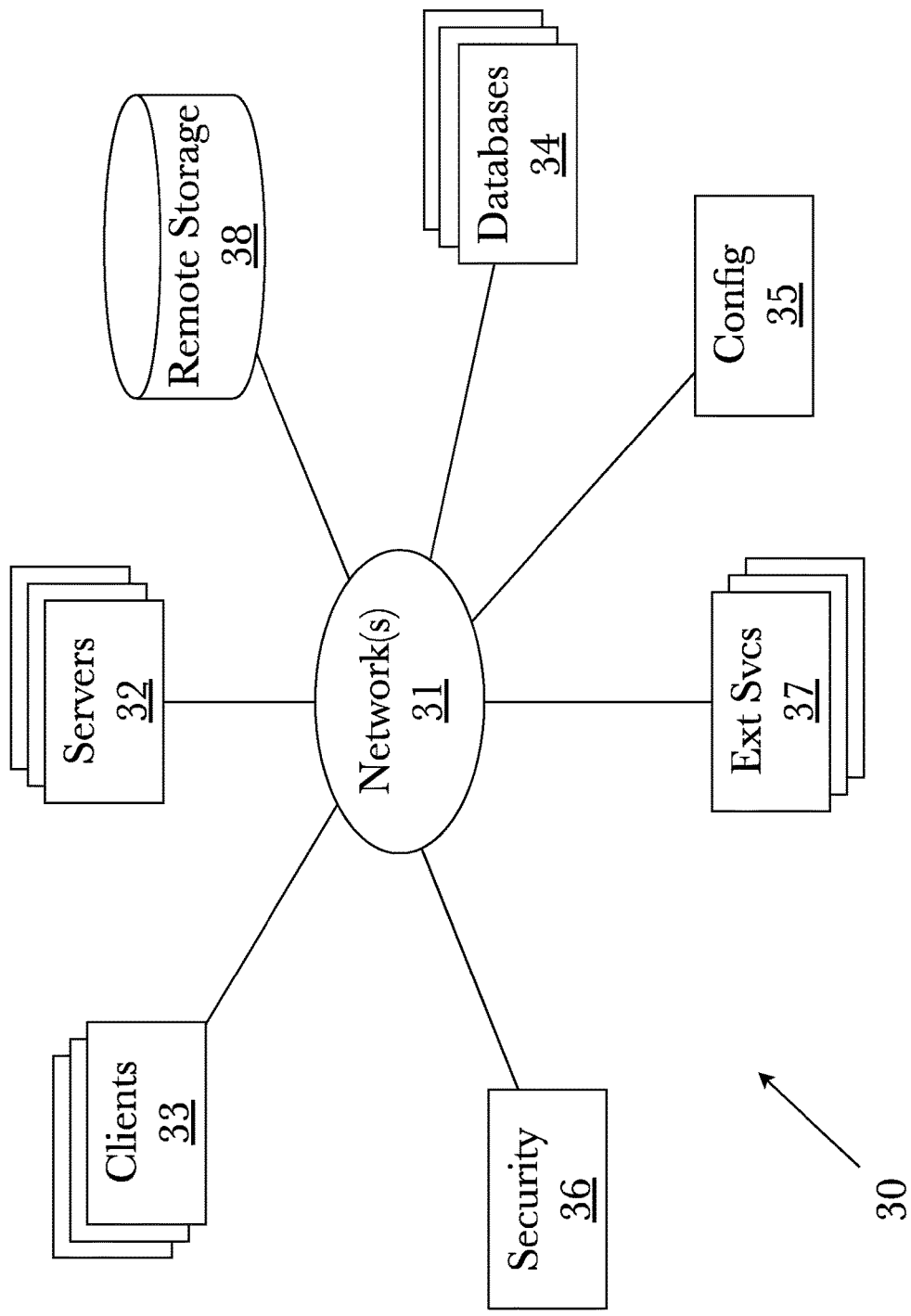
FIG. 12 is a block diagram showing an exemplary architectural arrangement of clients, servers, and external services.

In some aspects, systems may be implemented on a distributed computing network, such as one having any number of clients and/or servers. Referring now to FIG. 12, there is shown a block diagram depicting an exemplary architecture 30 for implementing at least a portion of a system according to one aspect on a distributed computing network. According to the aspect, any number of clients 33 may be provided. Each client 33 may run software for implementing client-side portions of a system; clients may comprise a system 20 such as that illustrated in FIG. 11. In addition, any number of servers 32 may be provided for handling requests received from one or more clients 33. Clients 33 and servers 32 may communicate with one another via one or more electronic networks 31, which may be in various aspects any of the Internet, a wide area network, a mobile telephony network (such as CDMA or GSM cellular networks), a wireless network (such as WiFi, WiMAX, LTE, and so forth), or a local area network (or indeed any network topology known in the art; the aspect does not prefer any one network topology over any other). Networks 31 may be implemented using any known network protocols, including for example wired and/or wireless protocols.

In addition, in some aspects, servers 32 may call external services 37 when needed to obtain additional information, or to refer to additional data concerning a particular call. Communications with external services 37 may take place, for example, via one or more networks 31. In various aspects, external services 37 may comprise web-enabled services or functionality related to or installed on the hardware device itself. For example, in one aspect where client applications 24 are implemented on a smartphone or other electronic device, client applications 24 may obtain information stored in a server system 32 in the cloud or on an external service 37 deployed on one or more of a particular enterprise's or user's premises. In addition to local storage on servers 32, remote storage 38 may be accessible through the network(s) 31.

In some aspects, clients 33 or servers 32 (or both) may make use of one or more specialized services or appliances that may be deployed locally or remotely across one or more networks 31. For example, one or more databases 34 in either local or remote storage 38 may be used or referred to by one or more aspects. It should be understood by one having ordinary skill in the art that databases in storage 34 may be arranged in a wide variety of architectures and using a wide variety of data access and manipulation means. For example, in various aspects one or more databases in storage 34 may comprise a relational database system using a structured query language (SQL), while others may comprise an alternative data storage technology such as those referred to in the art as "NoSQL" (for example, HADOOP CASSANDRA™, GOOGLE BIGTABLE™, and so forth). In some aspects, variant database architectures such as column-oriented databases, in-memory databases, clustered databases, distributed databases, or even flat file data repositories may be used according to the aspect. It will be appreciated by one having ordinary skill in the art that any combination of known or future database technologies may be used as appropriate, unless a specific database technology or a specific arrangement of components is specified for a particular aspect described herein. Moreover, it should be appreciated that the term "database" as used herein may refer to a physical database machine, a cluster of machines acting as a single database system, or a logical database within an overall database management system. Unless a specific meaning is specified for a given use of the term "database", it should be construed to mean any of these senses of the word, all of which are understood as a plain meaning of the term "database" by those having ordinary skill in the art.

Similarly, some aspects may make use of one or more security systems 36 and configuration systems 35. Security and configuration management are common information technology (IT) and web functions, and some amount of each are generally associated with any IT or web systems. It should be understood by one having ordinary skill in the art that any configuration or security subsystems known in the art now or in the future may be used in conjunction with aspects without limitation, unless a specific security 36 or configuration system 35 or approach is specifically required by the description of any specific aspect.

Figure 13:
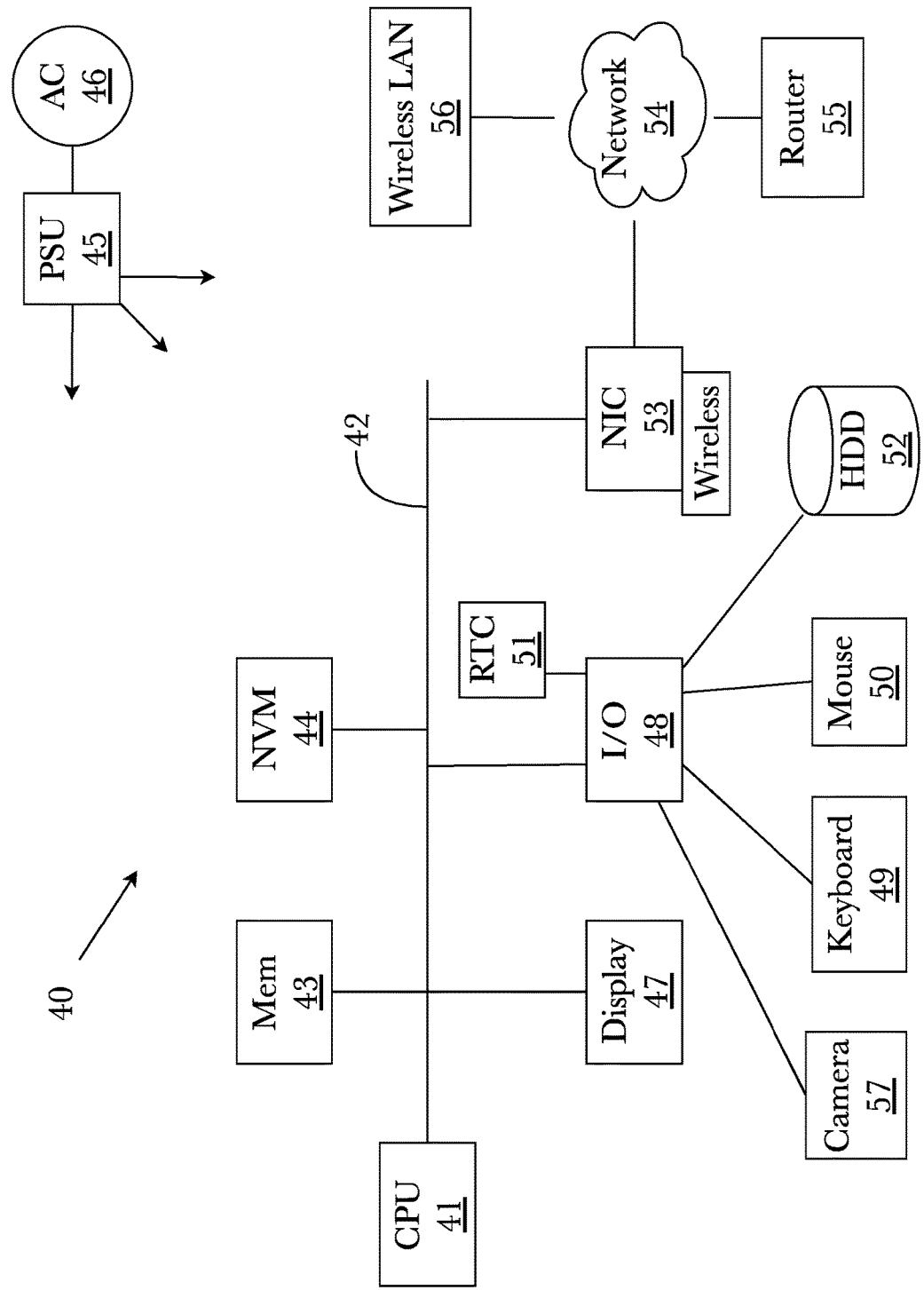
FIG. 13 is another block diagram illustrating an exemplary hardware architecture of a computing device.

FIG. 13 shows an exemplary overview of a computer system 40 as may be used in any of the various locations throughout the system. It is exemplary of any computer that may execute code to process data. Various modifications and changes may be made to computer system 40 without departing from the broader scope of the system and method disclosed herein. Central processor unit (CPU) 41 is connected to bus 42, to which bus is also connected memory 43, nonvolatile memory 44, display 47, input/output (I/O) unit 48, and network interface card (NIC) 53. I/O unit 48 may, typically, be connected to peripherals such as a keyboard 49, pointing device 50, hard disk 52, real-time clock 51, a camera 57, and other peripheral devices. NIC 53 connects to network 54, which may be the Internet or a local network, which local network may or may not have connections to the Internet. The system may be connected to other computing devices through the network via a router 55, wireless local area network 56, or any other network connection. Also shown as part of system 40 is power supply unit 45 connected, in this example, to a main alternating current (AC) supply 46. Not shown are batteries that could be present, and many other devices and modifications that are well known but are not applicable to the specific novel functions of the current system and method disclosed herein. It should be appreciated that some or all components illustrated may be combined, such as in various integrated applications, for example Qualcomm or Samsung system-on-a-chip (SOC) devices, or whenever it may be appropriate to combine multiple capabilities or functions into a single hardware device (for instance, in mobile devices such as smartphones, video game consoles, in-vehicle computer systems such as navigation or multimedia systems in automobiles, or other integrated hardware devices).

In various embodiments, functionality for implementing systems or methods of the present invention may be distributed among any number of client and/or server components. For example, various software modules may be implemented for performing various functions in connection with the present invention, and such modules may be variously implemented to run on server and/or client components.

The skilled person will be aware of a range of possible modifications of the various embodiments described above. Accordingly, the present invention is defined by the claims and their equivalents.

What is claimed is:

1. A system for multi-stage brain-computer interface training and profile configuration selection, comprising:
   one or more brain activity sensors;
   a neural network configured to identify patterns of brain activity corresponding to intended movements in virtual reality environments;
   a pre-pre-game training engine comprising a first plurality of programming instructions stored in a memory of, and operating on a processor of, a computing device, wherein the first plurality of programming instructions, when operating on the processor, cause the computing device to:
      display one or more computer-related training exercises to a user, each training exercise comprising a first virtual reality environment, a human avatar, and a task for the human avatar to perform in the first virtual reality environment;
      prompt the user to attempt to complete the task using the avatar in the first virtual reality environment while physically mimicking the same movements in the real world;
      prompt the user to repeat the attempt to complete the task using the avatar in the virtual reality environment without physically mimicking the same movements in the real world;
      record brain activity from the one or more brain activity sensors while the user completes the training exercises;
      use the neural network to compare the user's brain activity recorded while completing the training exercises with physical movement to the user's brain activity recorded while completing the training exercises without movement to identify patterns of recorded brain activity that correspond most closely with the avatar's successful completion of the tasks in the virtual reality environment;
   create and store a user profile for the user based on the identified patterns of recorded brain activity;
   process a plurality of user profiles through the neural network to identify commonalities across users in identified patterns of brain activity related to the training exercises;
   store the identified commonalities as sets of profile configurations for specific activities in the first virtual reality environment; and
   a real-time profile configuration selection engine comprising at least a second plurality of programming instructions stored in the memory of, and operating on the processor of, the computing device, wherein the second plurality of programming instructions, when operating on the processor, cause the computing device to:
      record brain activity from the one or more brain activity sensors while the user engages in activity in a second virtual reality environment which has been configured to be controlled by a brain-computer interface;
      process the recorded brain activity through the neural network to identify patterns of brain activity associated with the activity in the second virtual reality environment;
      compare the identified patterns of brain activity for the activity in the second virtual reality environment to the stored profile configurations for specific activities in the first virtual reality environment; and
      select one or more profile configurations for use based on closeness of fit between the patterns of brain activity for the activity in the second virtual reality environment to the patterns of brain activity for a similar activity in the stored profile configurations for specific activities in the first virtual reality environment.

2. The system of claim 1, wherein the neural network, pre-pre-game training engine, and real-time profile configuration selection are located on, and accessible through, a networked server.

3. A method for multi-stage brain-computer interface training and profile configuration selection, comprising the steps of:
   displaying one or more computer-related training exercises to a user, each training exercise comprising a first virtual reality environment, a human avatar, and a task for the human avatar to perform in the first virtual reality environment;

prompting the user to attempt to complete the task using the avatar in the first virtual reality environment while physically mimicking the same movements in the real world;

prompting the user to repeat the attempt to complete the task using the avatar in the virtual reality environment without physically mimicking the same movements in the real world;

recording brain activity from one or more brain activity sensors while the user completes the training exercises;

using the neural network to compare the user's brain activity recorded while completing the training exercises with physical movement to the user's brain activity recorded while completing the training exercises without movement to identify patterns of recorded brain activity that correspond most closely with the avatar's successful completion of the tasks in the virtual reality environment;

creating and storing a user profile for the user based on the identified patterns of recorded brain activity;

processing a plurality of user profiles through a neural network to identify commonalities across users in identified patterns of brain activity related to the training exercises;

storing the identified commonalities as sets of profile configurations for specific activities in the first virtual reality environment;

recording brain activity from one or more brain activity sensors while the user engages in an activity in a second virtual reality environment which has been configured to be controlled by a brain-computer interface;

processing the recorded brain activity through the neural network to identify patterns of brain activity associated with the activity in the second virtual reality environment;

comparing the identified patterns of brain activity for the activity in the second virtual reality environment to the stored profile configurations for specific activities in the first virtual reality environment; and selecting one or more profile configurations for use based on closeness of fit between the patterns of brain activity for the activity in the second virtual reality environment to the patterns of brain activity for a similar activity in the stored profile configurations for specific activities in the first virtual reality environment.

4. The method of claim 3, further comprising the step of locating the neural network, pre-pre-game training engine, and real-time profile configuration selection on a networked server, and making them accessible through the networked server.

5. A system for multi-stage brain-computer interface training and profile configuration selection, comprising:
one or more brain activity sensors;
a neural network configured to identify patterns of brain activity corresponding to intended movements in virtual reality environments;
a pre-pre-game training engine comprising a first plurality of programming instructions stored in a memory of, and operating on a processor of, a computing device, wherein the first plurality of programming instructions, when operating on the processor, cause the computing device to:
display one or more computer-related training exercises to a first user, each training exercise comprising a first virtual reality environment, a human avatar, and a task for the human avatar to perform in the first virtual reality environment;

prompt the first user to attempt to complete the task using the avatar in the first virtual reality environment while physically mimicking the same movements in the real world;

prompt the first user to repeat the attempt to complete the task using the avatar in the virtual reality environment without physically mimicking the same movements in the real world;

record brain activity from the one or more brain activity sensors while the first user completes the training exercises;

use the neural network to compare the user's brain activity recorded while completing the training exercises with physical movement to the user's brain activity recorded while completing the training exercises without movement to identify patterns of recorded brain activity that correspond most closely with the avatar's successful completion of the tasks in the virtual reality environment;

create and store a user profile for the first user based on the identified patterns of recorded brain activity;

process a plurality of user profiles through the neural network to identify commonalities across users in identified patterns of brain activity related to the training exercises;

store the identified commonalities as sets of profile configurations for specific activities in the first virtual reality environment; and a real-time profile configuration selection engine comprising at least a second plurality of programming instructions stored in the memory of, and operating on the processor of, the computing device, wherein the second plurality of programming instructions, when operating on the processor, cause the computing device to:

record brain activity from the one or more brain activity sensors while a second user engages in an activity in a second virtual reality environment which has been configured to be controlled by a brain-computer interface;

process the recorded brain activity through the neural network to identify patterns of brain activity associated with the activity in the second virtual reality environment;

compare the identified patterns of brain activity for the activity in the second virtual reality environment to the stored profile configurations for specific activities in the first virtual reality environment; and select one or more profile configurations for use based on closeness of fit between the patterns of brain activity for the activity in the second virtual reality environment to the patterns of brain activity for a similar activity in the stored profile configurations for specific activities in the first virtual reality environment.

6. The system of claim 5, wherein the neural network, pre-pre-game training engine, and real-time profile configuration selection are located on, and accessible through, a networked server.

7. A method for multi-stage brain-computer interface training and profile configuration selection, comprising the steps of:

displaying one or more computer-related training exercises to a first user, each training exercise comprising a first virtual reality environment, a human avatar, and a task for the human avatar to perform in the first virtual reality environment;

prompting the first user to attempt to complete the task using the avatar in the first virtual reality environment while physically mimicking the same movements in the real world;

prompting the first user to repeat the attempt to complete the task using the avatar in the virtual reality environment without physically mimicking the same movements in the real world;

recording brain activity from one or more brain activity sensors while the first user completes the training exercises;

using the neural network to compare the first user's brain activity recorded while completing the training exercises with physical movement to the first user's brain activity recorded while completing the training exercises without movement to identify patterns of recorded brain activity that correspond most closely with the avatar's successful completion of the tasks in the virtual reality environment;

creating and storing a user profile for the first user based on the identified patterns of recorded brain activity;

processing a plurality of user profiles through a neural network to identify commonalities across users in identified patterns of brain activity related to the training exercises;

storing the identified commonalities as sets of profile configurations for specific activities in the first virtual reality environment;

recording brain activity for a second user from one or more brain activity sensors while the second user engages in an activity in a second virtual reality environment which has been configured to be controlled by a brain-computer interface;

processing the recorded brain activity through the neural network to identify patterns of brain activity associated with the activity in the second virtual reality environment;

comparing the identified patterns of brain activity for the activity in the second virtual reality environment to the stored profile configurations for specific activities in the first virtual reality environment; and selecting one or more profile configurations for use based on closeness of fit between the patterns of brain activity for the activity in the second virtual reality environment to the patterns of brain activity for a similar activity in the stored profile configurations for specific activities in the first virtual reality environment.

8. The method of claim 7, further comprising the step of locating the neural network, pre-pre-game training engine, and real-time profile configuration selection on a networked server, and making them accessible through the networked server.

* * * * *